(12) United States Patent
Doo et al.

(10) Patent No.: US 10,874,821 B2
(45) Date of Patent: Dec. 29, 2020

(54) RESPIRATORY GAS THERAPY

(71) Applicant: Fisher & Paykel Healthcare Limited, Auckland (NZ)

(72) Inventors: James Samuel Wong Doo, Auckland (NZ); Andrew John Partington, Auckland (NZ); Nordyn Alami, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 715 days.

(21) Appl. No.: 15/532,475

(22) PCT Filed: Dec. 3, 2015

(86) PCT No.: PCT/NZ2015/050204
§ 371 (c)(1),
(2) Date: Jun. 1, 2017

(87) PCT Pub. No.: WO2016/089224
PCT Pub. Date: Jun. 9, 2016

(65) Prior Publication Data
US 2017/0348505 A1    Dec. 7, 2017

Related U.S. Application Data

(60) Provisional application No. 62/086,922, filed on Dec. 3, 2014.

(51) Int. Cl.
*A61M 16/16*    (2006.01)
*A61M 16/00*    (2006.01)
(Continued)

(52) U.S. Cl.
CPC ........ *A61M 16/164* (2014.02); *A61M 11/042* (2014.02); *A61M 16/0057* (2013.01);
(Continued)

(58) Field of Classification Search
CPC .............. A61M 16/16; A61M 16/0057; A61M 16/164; A61M 16/186
See application file for complete search history.

(56) References Cited

U.S. PATENT DOCUMENTS

| 3,290,021 A | 12/1966 | Blachly et al. |
| 4,921,642 A | 5/1990 | Latorraca |

(Continued)

FOREIGN PATENT DOCUMENTS

| EP | 1666082 | 6/2006 |
| EP | 1818070 | 8/2007 |

(Continued)

OTHER PUBLICATIONS

Extended European Search Report, European Application No. EP 15865792.4, dated Jul. 4, 2018, in 8 pages.
(Continued)

*Primary Examiner* — Timothy A Stanis
*Assistant Examiner* — Cana A Gallegos
(74) *Attorney, Agent, or Firm* — Knobbe, Martens, Olson & Bear, LLP

(57) ABSTRACT

A gases humidifier includes a gases inlet and an outlet, a removable humidification chamber cartridge with a heater source adapted to vaporize fluid, and a metering arrangement adapted to connect to and transfer fluid from a fluid (Continued)

supply to the humidification chamber. A gases humidifier includes a humidification chamber adapted to vaporize fluid and a metering arrangement adapted to transfer fluid from a fluid supply to the humidification chamber.

21 Claims, 25 Drawing Sheets

(51) Int. Cl.
*A61M 11/04* (2006.01)
*F24F 6/08* (2006.01)
*A61M 16/10* (2006.01)
*A61M 16/08* (2006.01)

(52) U.S. Cl.
CPC .... *A61M 16/0066* (2013.01); *A61M 16/0816* (2013.01); *A61M 16/109* (2014.02); *A61M 16/16* (2013.01); *F24F 6/08* (2013.01); *A61M 16/1055* (2013.01); *A61M 16/1065* (2014.02); *A61M 16/1075* (2013.01); *A61M 16/1095* (2014.02); *A61M 16/161* (2014.02); *A61M 16/162* (2013.01); *A61M 2016/0027* (2013.01); *A61M 2016/0039* (2013.01); *A61M 2205/123* (2013.01); *A61M 2205/3334* (2013.01); *A61M 2205/3368* (2013.01); *A61M 2205/505* (2013.01); *A61M 2205/581* (2013.01); *A61M 2205/8206* (2013.01); *A61M 2206/14* (2013.01); *A61M 2209/084* (2013.01)

(56) References Cited

U.S. PATENT DOCUMENTS

| | | | |
|---|---|---|---|
| 6,095,505 A * | 8/2000 | Miller | A61M 16/1075 128/203.27 |
| 2002/0039487 A1 * | 4/2002 | Wang | F24F 6/10 392/395 |
| 2006/0033223 A1 * | 2/2006 | Mantell | A61M 13/003 261/158 |
| 2008/0302361 A1 * | 12/2008 | Snow | A61M 16/109 128/202.27 |
| 2009/0241948 A1 | 10/2009 | Clancy et al. | |
| 2011/0172487 A1 | 7/2011 | Khodak et al. | |

FOREIGN PATENT DOCUMENTS

| | | |
|---|---|---|
| GB | 2001245 | 1/1979 |
| GB | 2001248 | 1/1979 |
| WO | WO2002/000284 | 1/2002 |
| WO | WO 2016/036260 | 3/2016 |

OTHER PUBLICATIONS

Examination Report for EP Application No. 15 865 724.4 dated Feb. 27, 2019 in 7 pages.
International Search Report for PCT/NZ2015/050204 dated Mar. 8, 2016 (6 pages).
Examination Report for Australian Application No. 2015355670 dated Dec. 13, 2019 in 4 pages.

* cited by examiner

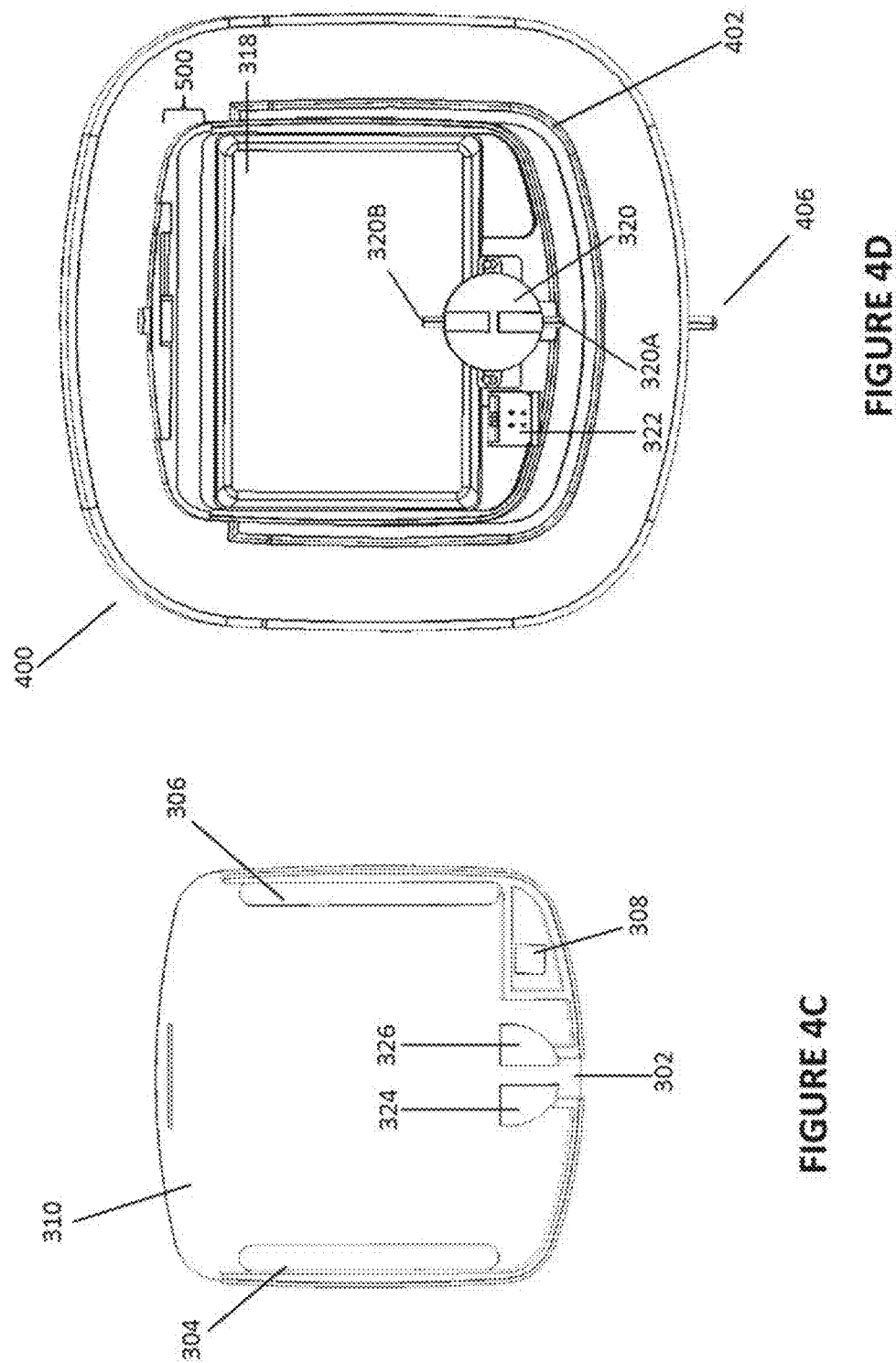

RESPIRATORY GAS THERAPY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure generally relates to respiratory gas therapy. More particularly, but not exclusively, the present disclosure relates to respiratory gas therapy systems with gas humidifiers.

DESCRIPTION OF THE RELATED ART

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes the threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient. A gases humidifier may be used to humidify gases being delivered to the patient.

SUMMARY OF INVENTION

Gases humidifiers can comprise a fluid reservoir adapted to store a quantity of humidification fluid (e.g. water) that can be used to humidify gases passing through the gases humidifier. A resistive heating element can be located under the fluid reservoir. Heat transmitted from the resistive heating element to the fluid increases the temperature of the fluid, encouraging vaporization and entrainment of the fluid in the gases stream passing through the gas humidifier. However with such a design, generally the entire mass of fluid in the fluid reservoir must increase in temperature before appreciable gains in output humidity can be realized. The heat energy required to heat such a fluid mass can be considerable and the type of resistive heating element used along with the power supply for the resistive heating element can be important design choices. Additionally, the thermal hysteresis of the mass of fluid within the fluid reservoir reduces the ability of such a gases humidifier to quickly change output humidity in response to changing input gas flow rates or pressures (for example, changing flow rates or pressures that might occur when using positive airway pressure with pressure ramping, bi-level pressure or expiratory pressure relief features). Such fluid reservoirs can be bulky and can have a considerable effect on the size and aesthetic appeal of the gases humidifier. As the inner surfaces of the fluid reservoir are in contact with fluid in use, replacing the entire fluid reservoir to manage the risk of pathogenic contamination can become inconvenient and expensive. Solutions for the above difficulties are sought.

It is an object of the present invention to provide an improved respiratory therapy system.

Thus, in accordance with certain features, aspects and advantages of at least one of the embodiments disclosed herein, in one aspect a gases humidifier is disclosed. The gases humidifier comprises a humidification chamber adapted to vaporize fluid and a metering arrangement adapted to transfer fluid from a fluid supply to the humidification chamber. At least a part of the metering arrangement lies within the gases humidifier.

In some configurations, at least a part of the metering arrangement lies within the humidification chamber. In some such configurations only an outlet of the metering arrangement lies within the humidification chamber.

In some configurations, the metering arrangement comprises a pump.

In some configurations, the humidification chamber comprises a heater adapted to heat the fluid. In some such configurations, the gases humidifier additionally comprises a thermally conductive element positioned over the heater. In some such configurations, the metering arrangement is configured to transfer liquid directly to the thermally conductive element. In some such configurations, an outlet of the metering arrangement is positioned directly over the thermally conductive element.

If the thermally conductive element is used, in some configurations the humidification chamber defines a cavity adapted to accept the thermally conductive element. In some such configurations the thermally conductive element is slideably locatable within the cavity. In some such configurations, the gases humidifier further comprises a locking engagement arrangement configured to retain the thermally conductive element within the cavity. In some such configurations, the locking engagement arrangement comprises open and closed positions, wherein the locking engagement arrangement may be detached from the gases humidifier when in the open position to allow access to the thermally conductive element.

In another aspect a gases humidifier is disclosed. The gases humidifier comprises a gases inlet; a gases outlet; a humidification chamber interposed between the gases inlet and the gases outlet, the humidification chamber adapted to vaporize a liquid such that it is transferred to a gas stream passing through the humidifier from the gases inlet to the gases outlet; and a metering arrangement adapted to transfer the liquid from a liquid supply to the humidification chamber; wherein at least a part of the metering arrangement lies within the humidification chamber.

In some configurations, only an outlet of the metering arrangement lies within the humidification chamber.

In some configurations, the metering arrangement comprises a pump.

In some configurations, the humidification chamber comprises a heater adapted to heat the fluid.

In some configurations, a thermally conductive element positioned over the heater.

In some configurations, the metering arrangement is configured to transfer liquid directly to the thermally conductive element.

In some configurations, an outlet of the metering arrangement is positioned directly over the thermally conductive element.

In some configurations, the humidification chamber defines a cavity adapted to accept the thermally conductive element.

In some configurations, the thermally conductive element is slideably locatable within the cavity.

In some configurations there is a locking engagement arrangement configured to retain the thermally conductive element within the cavity.

In some configurations, the locking engagement arrangement comprises open and closed positions, and wherein the locking engagement arrangement may be detached from the gases humidifier when in the open position to allow access to the thermally conductive element.

In another aspect a gases humidifier is disclosed. The gases humidifier comprises an aperture defined by a humidification chamber adapted to vaporize fluid; a humidification element slideably locatable within the aperture; and a locking engagement arrangement configured to retain the humidification element within the aperture; wherein the locking engagement arrangement comprises open and closed positions, and wherein the locking engagement arrangement is configured to be detached from the gases humidifier when in the open position to allow access to the humidification element. In some configurations, the humidification element is a thermally conductive element.

In some configurations, there is also a metering arrangement adapted to transfer fluid from a fluid supply, wherein the metering arrangement is configured to deposit fluid onto the thermally conductive element when the thermally conductive element is present within the aperture.

In some configurations, at least a part of the metering arrangement lies within the humidification chamber.

In some configurations, only an outlet of the metering arrangement lies within the humidification chamber.

In some configurations, the metering arrangement comprises a pump.

In another aspect a respiratory therapy system is disclosed. The respiratory therapy system comprises a flow generator; and a gases humidifier detachably connectable to the flow generator, the gases humidifier comprising: a humidification chamber adapted to vaporize fluid; and a metering arrangement adapted to transfer fluid from a fluid supply to the humidification chamber; wherein at least a part of the metering arrangement lies within the gas humidifier. In some configurations, the gases humidifier is detachably connectable to a bottom surface of the flow generator in such a way that the footprint of the flow generator is substantially maintained.

In some configurations, there is also a fluid reservoir comprising a seat in which the gases humidifier may be located.

In some configurations, the gases humidifier is detachably connectable to a bottom surface of the flow generator in such a way that the footprint of the flow generator is substantially maintained.

In some configurations, the respiratory therapy system further comprises a fluid reservoir comprising a seat in which the gases humidifier may be located.

In another aspect a gases humidifier is disclosed comprising: a gases inlet and an outlet, a removable humidification chamber cartridge with a heater source adapted to vaporize fluid; and a metering arrangement adapted to connect to and transfer fluid from a fluid supply to the humidification chamber.

In some configurations, one or more sensors to measure temperature and/or humidity.

In some configurations, the heater source is a heating element integrated in or forming part of the humidification chamber cartridge.

In some configurations, the heater source is a PCB heater, ECP structure, or combination of PCB and ECP structure.

In some configurations, the pump is connected to a fluid supply.

In some configurations, there is also a fluid supply.

In some configurations, there is also an external or internal power source.

In some configurations, the metering arrangement is a pump or a valve.

BRIEF DESCRIPTION OF THE DRAWINGS

Specific embodiments and modifications thereof will become apparent to those skilled in the art from the detailed description herein having reference to the figures that follow, of which:

FIG. 4C shows a bottom plan view of a portion of a gases humidifier.

FIG. 4D shows a top plan view of a portion of a gases humidifier.

DETAILED DESCRIPTION

Figure 1:
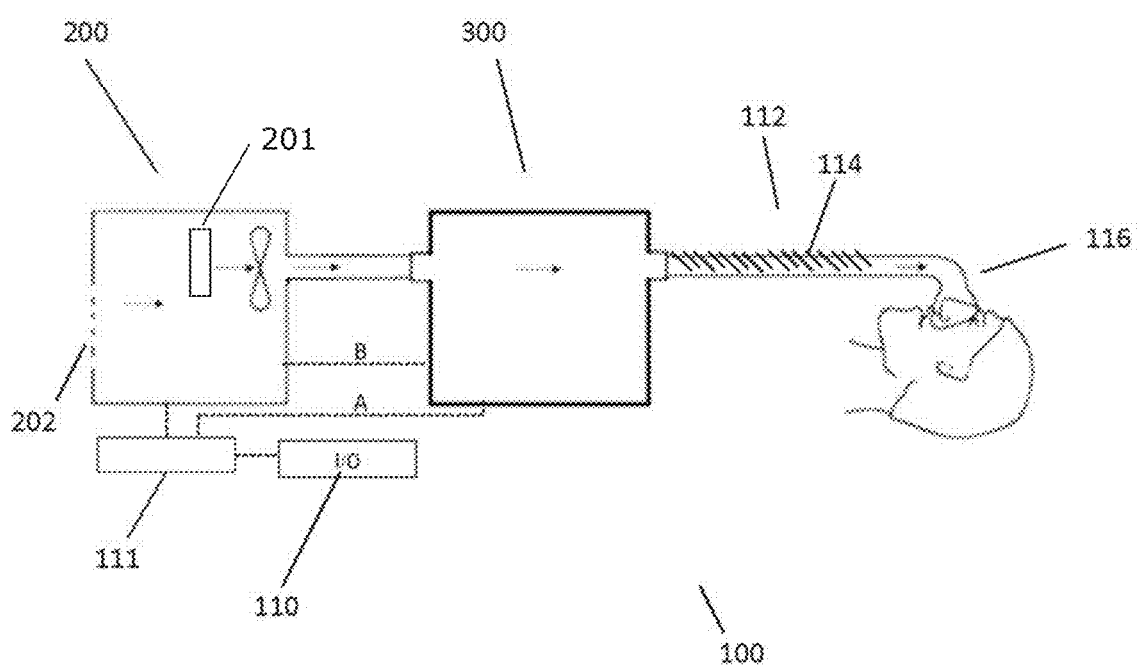
FIG. 1 shows a schematic diagram of a respiratory therapy system.

With reference to the non-limiting exemplary embodiment illustrated in FIG. 1, a respiratory therapy system 100 is shown. The respiratory therapy system 100 comprises a flow generator 200. The flow generator 200 comprises a blower apparatus 201, such as a PAP device. The flow generator 200 receives gases from a gases inlet 202 and transfers them to a gases humidifier 300. The gases humidifier 300 heats and humidifies the gases. Heated and humidified gases are passed from a humidifier outlet to a gases conduit 112. The gases conduit 112 comprises a heater 114. The heater 114 reduces or prevents the condensation of moisture along the walls of the gases conduit 112. Gases are passed from the gases conduit 112 to a patient interface 116 through which they are delivered to a user. The respiratory therapy system 100 comprises a controller 111 that controls the operation of the flow generator 200. The controller 111 also controls the operation of the gases humidifier 300. The respiratory therapy system 100 comprises an input/output (I/O) module 110. The I/O module 110 comprises a way for a user to interact with and set parameters for the flow generator 200 and/or gases humidifier 300 (e.g. through the controller 111) as well as receive information regarding the operation of the respiratory therapy system 100 and/or its components. The I/O module 110 may comprise, for example, buttons, knobs, dials, switches, levers, touch screens, speakers, displays and/or other input or output elements. In other configurations, the gas conduit 112 may not have a heater 114. In some configurations, the controller 111 may communicate directly with both the flow generator 200 and the gases humidifier 300 (along data pathway 'A' as seen in FIG. 1). In other configurations, the controller 111 may communicate with the flow generator 200, and may only communicate with the gases humidifier 300 only when the flow generator 200 is connected to the gases humidifier 300 (e.g. along data pathway 'B' representing a data linkage between the flow generator 200 and the gases humidifier 300 as seen in FIG. 1).

The flow generator 200 and gases humidifier 300 may be part of an integrated flow delivery system or may share a housing. In other configurations, the flow generator 200 may comprise elements other than PAP devices, including but not limited to high flow therapy devices or ventilation devices. If a PAP device is utilized, the PAP device may comprise a number of PAP device variants, including but not limited to continuous positive airway pressure (CPAP) devices, automatically adjusting positive airway pressure (APAP or AutoPAP) devices, or bi-level positive airway pressure (BiPAP or bi-level PAP) devices. The patient interface 116 comprises a mask adapted to seal about and channel gases to the nose and/or mouth of the user. In other configurations, the patient interface 116 may comprise a semi-sealing or non-sealing interface. In other configurations the patient interface 116 may comprise an oral mask, an oro-nasal mask, a full face mask, a nasal pillows mask, a nasal cannula, an endotracheal mask or tube, combinations of the above, or other gas conveying elements, apparatus or systems.

Figure 2A:
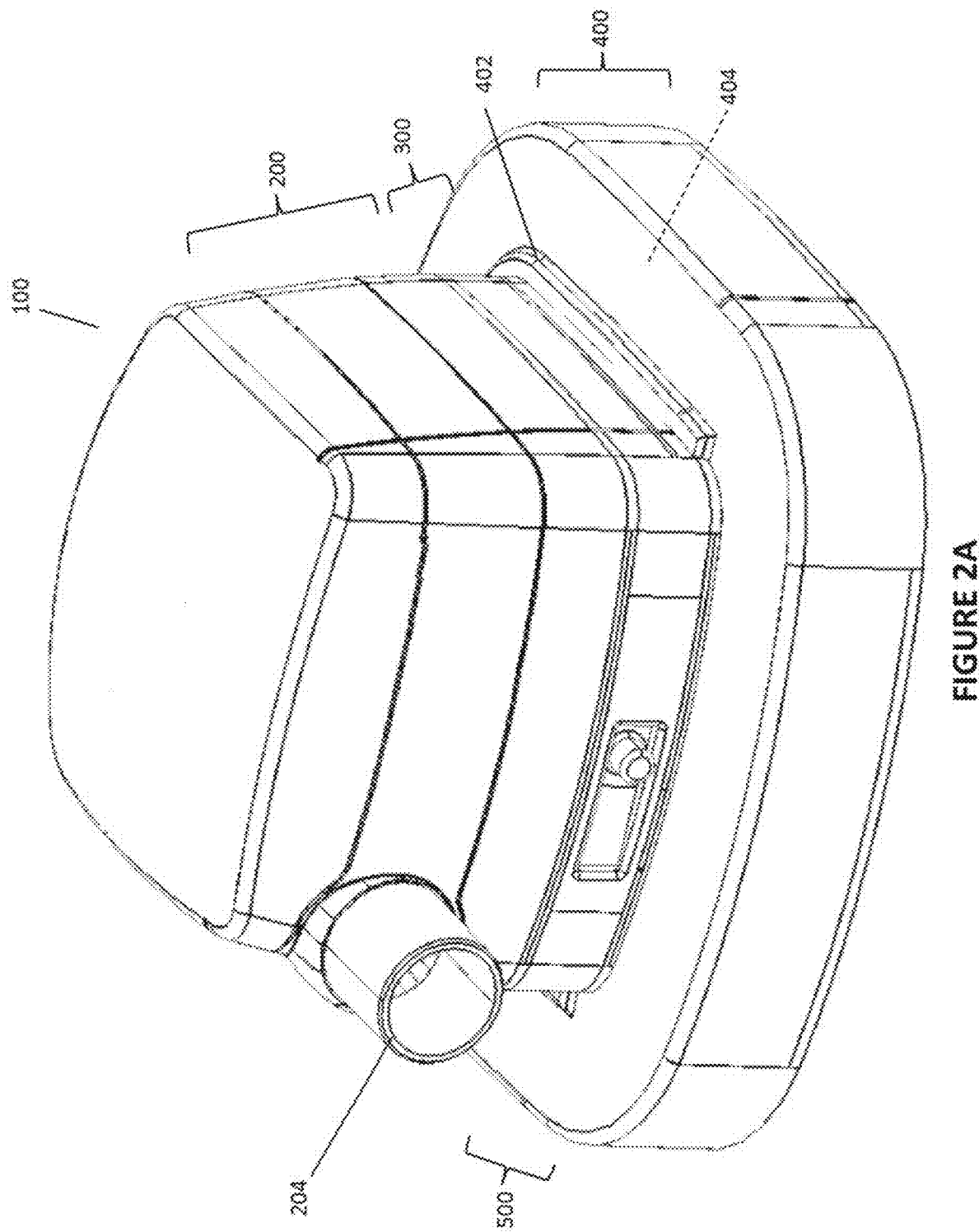
FIG. 2A shows a front perspective view of a respiratory therapy system.
Figure 2B:
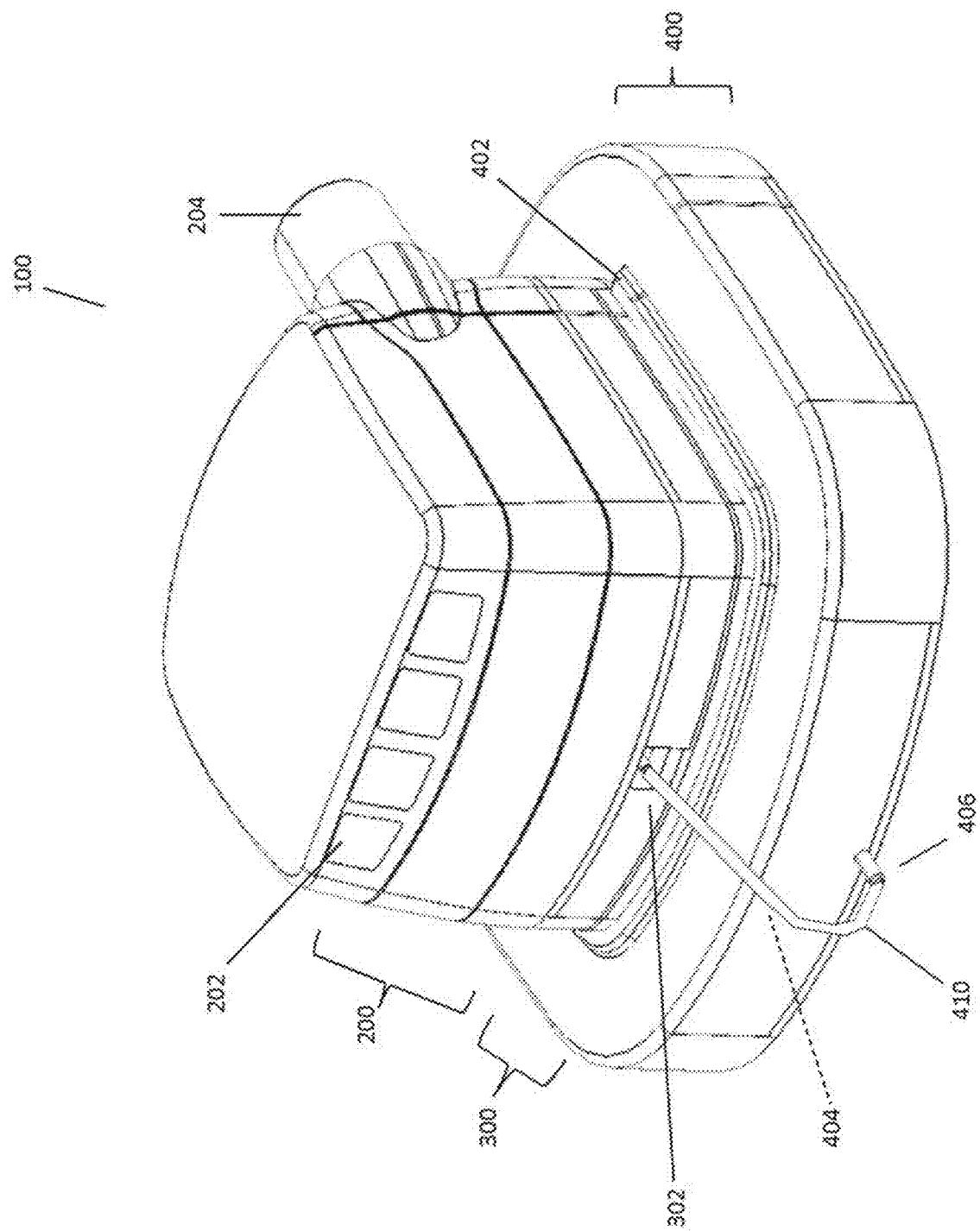
FIG. 2B shows a rear perspective view of a respiratory therapy system.

FIGS. 2A and 2B show a non-limiting exemplary respiratory therapy system 100 that may be used with the configuration illustrated in FIG. 1. As shown, the respiratory therapy system 100 comprises a flow generator 200. The flow generator 200 comprises a gases inlet 202 (see FIG. 2B). The gases inlet 202 comprises a series of inlet apertures positioned on a rear portion of the housing of the flow generator 200. The inlet apertures may be covered or insulated with noise attenuating structures or elements (including but not limited to open cell foams or 'honeycomb' structures) to reduce noise generated by flow passing into the flow generator 200 through the gases inlet 202. In some configurations, gas filters may be positioned at or near the gases inlet 202. The gas filters may remove contaminants or pollutants from the incoming gas stream. The gas filters may be anti-pathogenic (e.g. anti-bacterial, anti-viral, anti-fungal, etc). The flow generator 200 additionally comprises a gases outlet 204 through which gases leave the flow generator 200 and pass through a gases conduit (for example, the gases conduit 112 described elsewhere in this disclosure with reference to FIG. 1). Inside the housing is a blower apparatus. The blower apparatus may include, for example, one of the blower apparatus described in commonly-owned WO2013/009193, the entire content of which is hereby incorporated by reference in its entirety.

The illustrated flow generator 200 is not to be taken as limiting, and other configurations are envisioned. For example, in some configurations, the gases inlet 202 may comprise a single elongate aperture. In other configurations, the gases inlet 202 may comprise a plurality of relatively small apertures. In some configurations, a gases filter may be positioned downstream of the gases inlet 202 to remove contaminants or particulates in the gases supply (e.g. ambient air). In some configurations, the flow generator 200 may comprise a container of pressurized gases or a bellows arrangement instead of or in addition to a mechanical blower. In some configurations, the flow generator 200 may comprise a radial gases outlet or an axial gases outlet rather than the tangential gases outlet 204 shown in FIGS. 2A-2B.

The respiratory therapy system 100 additionally comprises a gases humidifier 300. The gases humidifier 300 is a modular construction and is detachably fixable to the flow generator 200. The gases humidifier 300 may, for example, be connected to the flow generator 200 through the use of various arrangements or devices, including but not limited to latch/catch arrangements, bayonet-style fittings and protrusion/recess connection arrangements. The footprint of the gases humidifier 300 is substantially similar to the footprint of the flow generator 200. In other words, the combined footprint of the flow generator 200 and the gases humidifier 300 is not substantially greater than either of the two components with respect to the area taken up by the combined unit on a flat space on, for example, a horizontal stand or support (e.g. a night stand or table). The gases humidifier 300 shown is a pass-over type humidifier where a gas stream moving through the gases humidifier 300 passes along a body of fluid and increases in humidity as it passes along the body of fluid. The gases humidifier 300 comprises a fluid inlet aperture 302 (described elsewhere in this disclosure). Components of the gases humidifier 300 can be accessed through a locking engagement arrangement 500 (described elsewhere in this disclosure).

In other configurations, the gases humidifier 300 may be integrated with the flow generator 200, or share a housing with the flow generator 200. In some configurations, the illustrated flow generator 200 may not be present, and gases from a remote source may be channeled through the gases humidifier 300. Seals may be present on the flow generator 200 and/or gases humidifier 300 to ensure a sealed gases passageway between the flow generator 200 and the gases humidifier 300.

The gases humidifier 300 rests on a fluid reservoir 400. The fluid reservoir 400 comprises a raised portion or seat 402 extending from a top surface of the fluid reservoir 400. The raised portion 402 defines a space in which the gases humidifier 300 may be placed. The fluid reservoir 400 comprises an internal space 404 configured to hold a quantity of fluid. A fluid outlet 406 is positioned on one side of the fluid reservoir 400. The fluid outlet 406 comprises an open cylindrical projection in communication with the internal space 404. The cylindrical projection of the fluid outlet 406 interfaces with a fluid tubing 410 that extends between the cylindrical projection and the fluid inlet aperture 302 (described elsewhere in this disclosure). The fluid tube can be integrated into the reservoir or in the humidifier if the humidifier docks onto the water reservoir. The fluid reservoir 400 additionally comprises a fill aperture 408 (see FIG. 3) through which fluid may be transferred into the internal space 404.

In other configurations, the raised portion 402 or a separate fastening arrangement or device may be configured to releasably join the gases humidifier 300 to the fluid reservoir 400. In other configurations, the gases humidifier 300 may be integrated with the fluid reservoir 400, or may share a housing with the fluid reservoir 400. The gases humidifier 300 may be permanently fixed to the fluid reservoir 400. In other configurations, the fluid reservoir 400 may not have a fill aperture 408, and fluid may both enter and exit the fluid reservoir 400 through the fluid inlet aperture 406. In still other configurations the fluid reservoir 400 may not be present, and fluid may be delivered to the fluid inlet aperture 302 of the gases humidifier 300 from a remote reservoir via a section of fluid tubing 410 (e.g. from a water bag suspended above the flow generator 200 and/or gases humidifier 300. In some configurations, the fluid reservoir 400 may instead be joined to the top of the gases humidifier 300, or to the top of the flow generator 200. Although in the illustrated configuration the fluid reservoir 400 comprises a larger footprint than the flow generator 200 or the gases humidifier 300, in other configurations the fluid reservoir 400 may comprise the same or a similar footprint.

Figure 3:
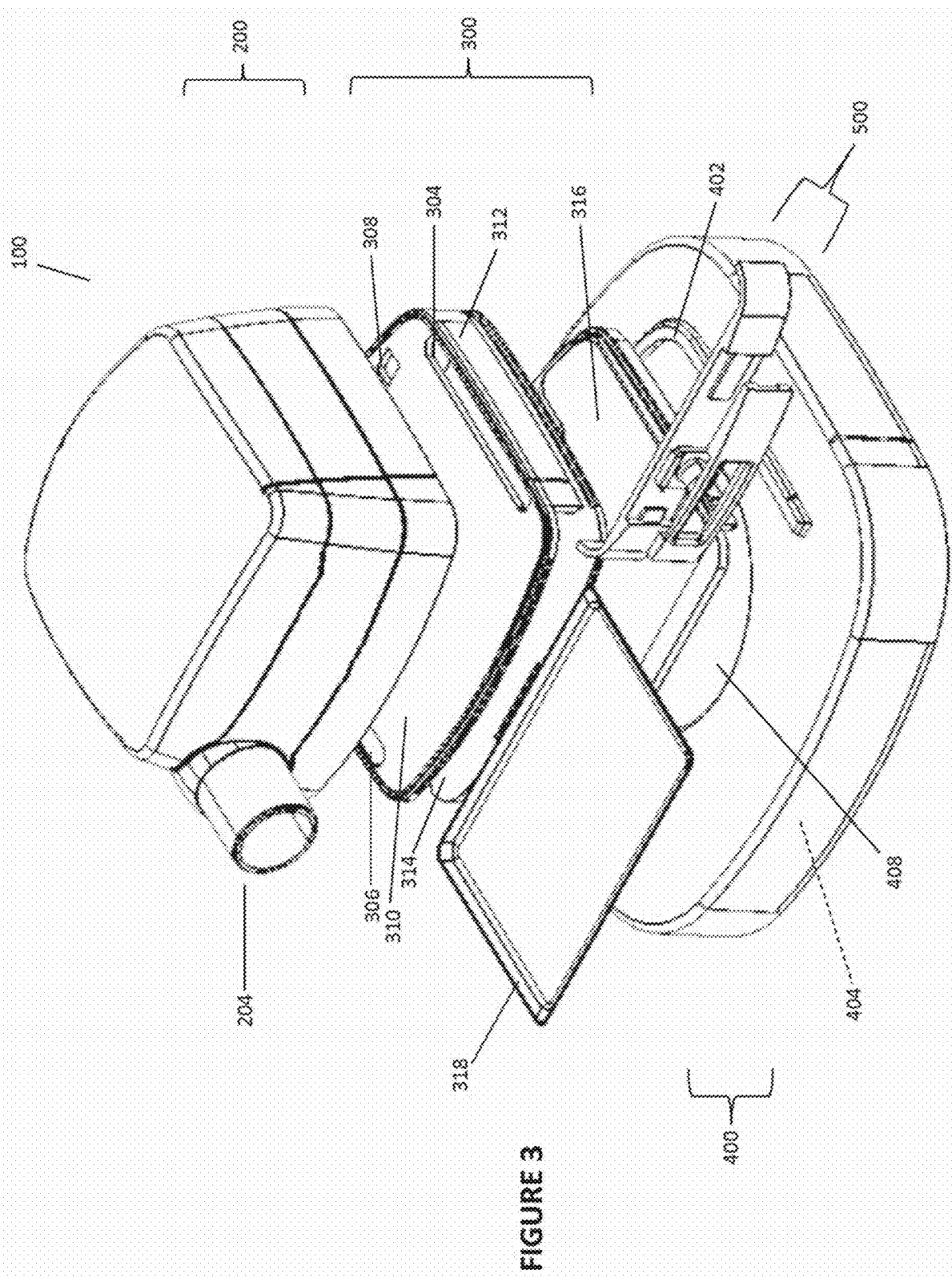
FIG. 3 shows an exploded front perspective view of a respiratory therapy system.

FIG. 3 illustrates an exploded view of the respiratory therapy system 100 shown in FIGS. 2A and 2B. As shown, the gases humidifier 300 comprises a top portion 310, a bottom portion 314, and a side wall 312. Gases humidifier inlet 304 and gases humidifier outlet 306 openings lie on the top portion 310 and allow gas to pass from the flow generator 200 to a chamber or humidification region defined between the top and bottom portions 310, 314 and side wall 312. An aperture 308 is positioned on one side of the top portion 310 to allow for an electrical connector extending from the gases humidifier 300 to provide power to the flow generator 200, or vice versa, to allow an electrical connector extending from the flow generator 200 to provide power to the gases humidifier 300. A thermally conductive element 318 is removably insertable into the chamber defined between the top and bottom portions 310, 314. The thermally conductive element 318 takes the form of a tray that is slideably positionable within the chamber. A base component 316 lies under the bottom portion 314 and provides support to the gases humidifier 300. The base component 316 also cooperates with the locking engagement arrangement 500 to retain the thermally conductive element 318 within the chamber (described elsewhere in this disclosure).

In some configurations, baffles, walls or fins may be located in the flow generator 200 to compel flow passing through the flow generator 200 to move through the gases humidifier inlet 304. Other baffles, walls or fins may be located in the flow generator 200 to compel flow leaving the gases humidifier outlet 306 and re-entering the flow generator 200 to exit through the gases outlet 204. In some configurations, the chamber may comprise rails that guide the sliding motion of the thermally conductive element 318 into the chamber. The rails may extend inwardly into the chamber from the side wall 312. In other configurations, the chamber may comprise a structure adapted to force or urge the thermally conductive element 318 towards the bottom portion 314 to maximize heating efficiency (see following disclosure). In other configurations, the thermally conductive element 318 may be permanently fixed to the gases humidifier 300. For example, the thermally conductive element 318 could simply be a layer of thermally conductive material present on the surface of the bottom portion 314. If the bottom portion 314 comprises an electrical component (e.g. an electric heater) the thermally conductive material may also be electrically insulative. In other configurations, the thermally conductive element 318 may comprise a flat surface or a bowl shape rather than a tray shape. The thermally conductive element 318 may not necessarily be limited to moving slideably in and out of the chamber. In other configurations, the thermally conductive element 318 may be inserted into the chamber from a top or bottom aperture. In some configurations, either of the flow generator 200 or the gases humidifier 300 may be powered by a separate mains connection or battery. In some such configurations, no electrical connection links the flow generator 200 and the gases humidifier 300. In some configurations, the electrical connection linking the flow generator 200 and the gases humidifier 300 may include a data transfer linkage such that the same controller may be used to control both the flow generator 200 and the gases humidifier 300.

In some configurations, the thermally conductive element 318 may comprise fins or baffles that compel flow passing along the thermally conductive element 318 to move along a more tortuous path. In some configurations, the chamber may comprise fins or baffles that compel flow passing through the chamber to move along a more tortuous path. Fins or baffles present on the thermally conductive element 318 and/or in the chamber may improve the efficacy of the gases humidifier 300. In some configurations, the thermally conductive element 318 may comprise a wicking structure. The wicking structure may cause fluid deposited on the thermally conductive element 318 to be spread out over the surface of the thermally conductive element 318. The wicking structure could, for example, comprise natural or artificial sponge, melamine foam, or a water sorbent material. In some configurations, the thermally conductive element 318 may comprise surface details or features that promote the spread of fluid over the surface of the thermally conductive element 318. For example, the thermally conductive element 318 could comprise microstructures including but not limited to microchannels, micro-size protrusions or micro-size recesses that promote the spread of liquid via capillary action. The microstructures on the thermally conductive element 318 could comprise one or more of the microstructure configurations disclosed in commonly-owned WO2014/003579 or commonly-owned WO2014/142677, the entire contents of each of which are hereby incorporated into this disclosure in their entirety.

The bottom portion 314 comprises a heater adapted to heat the thermally conductive element 318 present in the chamber. In the illustrated configuration, the heater comprises a printed circuit board. The printed circuit board receives electrical energy from the flow generator 200 though an electrical connector extending through the aperture 308. The electrical energy is used by the printed circuit board to generate heat which in turn is transmitted through the thermally conductive element 318 to heat fluids present on the thermally conductive element 318. The heated fluids are encouraged to evaporate and become entrained in the gases stream passing through the gases humidifier 300.

The heater may be maintained at a constant temperature or duty cycle dependent on one or more input parameters (received, for example, by the I/O module 110 described elsewhere in this disclosure with reference to FIG. 1), or may be controlled in a number of other ways. In other configurations, the heater may comprise a number of heating arrangements or apparatus, including but not limited to resistive heater elements, heating surfaces with etched or printed heating tracks, masses of material with in-mold heating devices, chemical heating systems, and wireless heating systems. In some configurations, a thermally conductive and/or electrically insulative layer may cover at least a section of the heater. The thermally conductive and/or electrically insulative layer may be overmoulded onto the heater. In some configurations, a three-layer construction may be used. A first thermally conductive and electrically insulative layer (first layer; for example, Kapton film) may be used to cover the heater. A second protective layer (for example, a stainless steel or aluminium film) may cover the first layer to protect the first layer from scratches or abrasions.

Figure 4A:
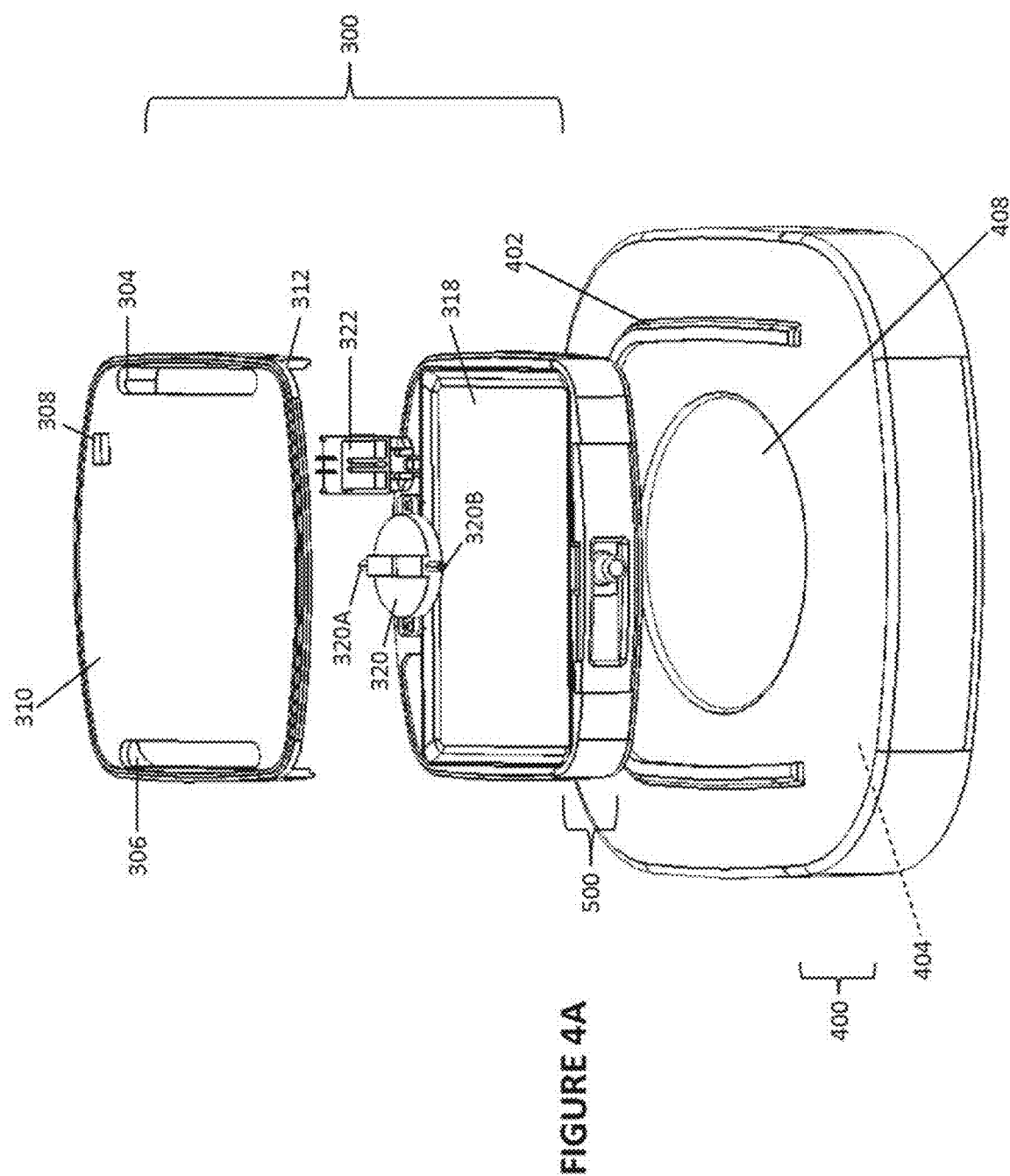
FIG. 4A shows an exploded elevated rear view of a gases humidifier.
Figure 4B:
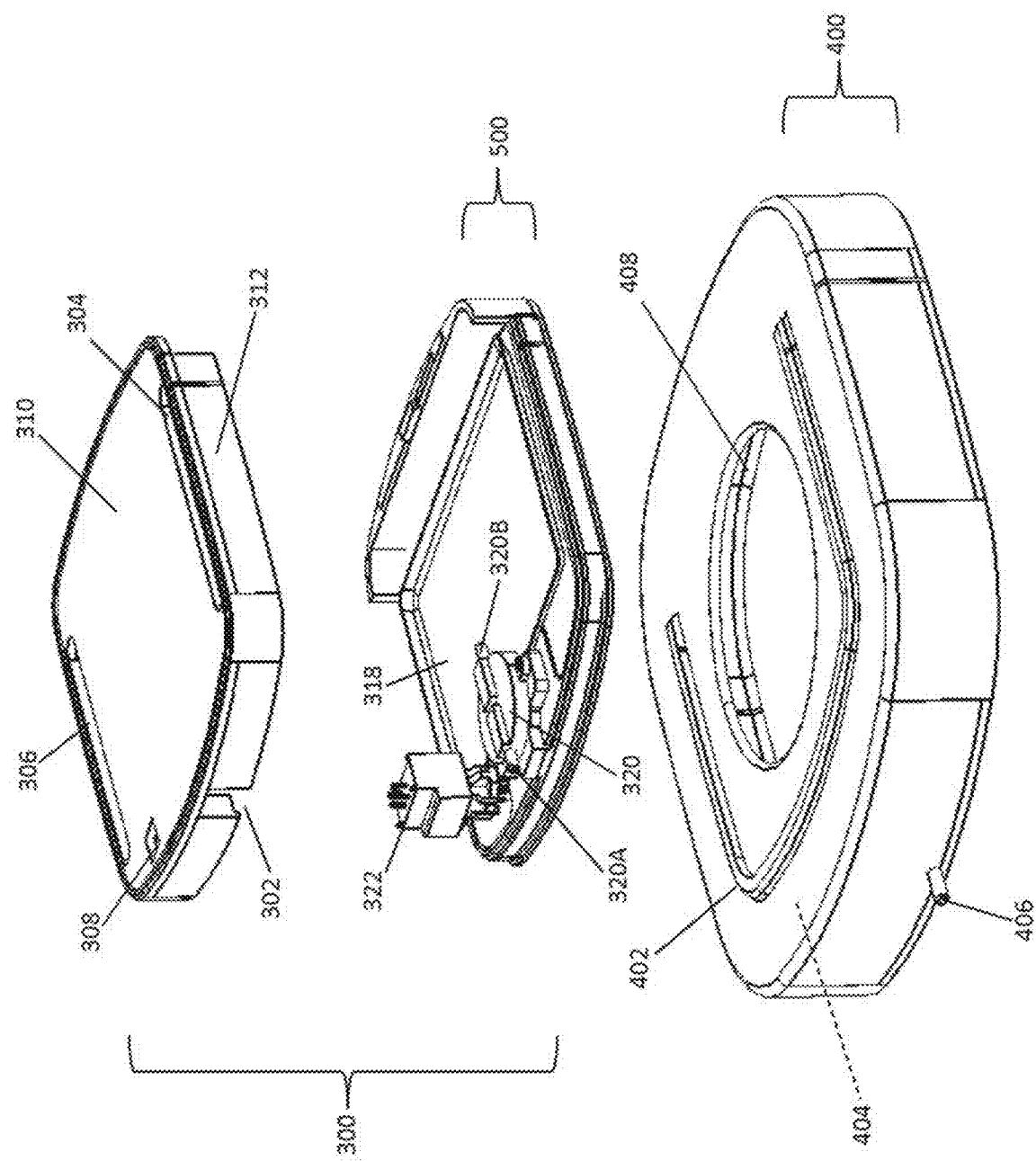
FIG. 4B shows an exploded perspective view of a gases humidifier.
Figure 5:
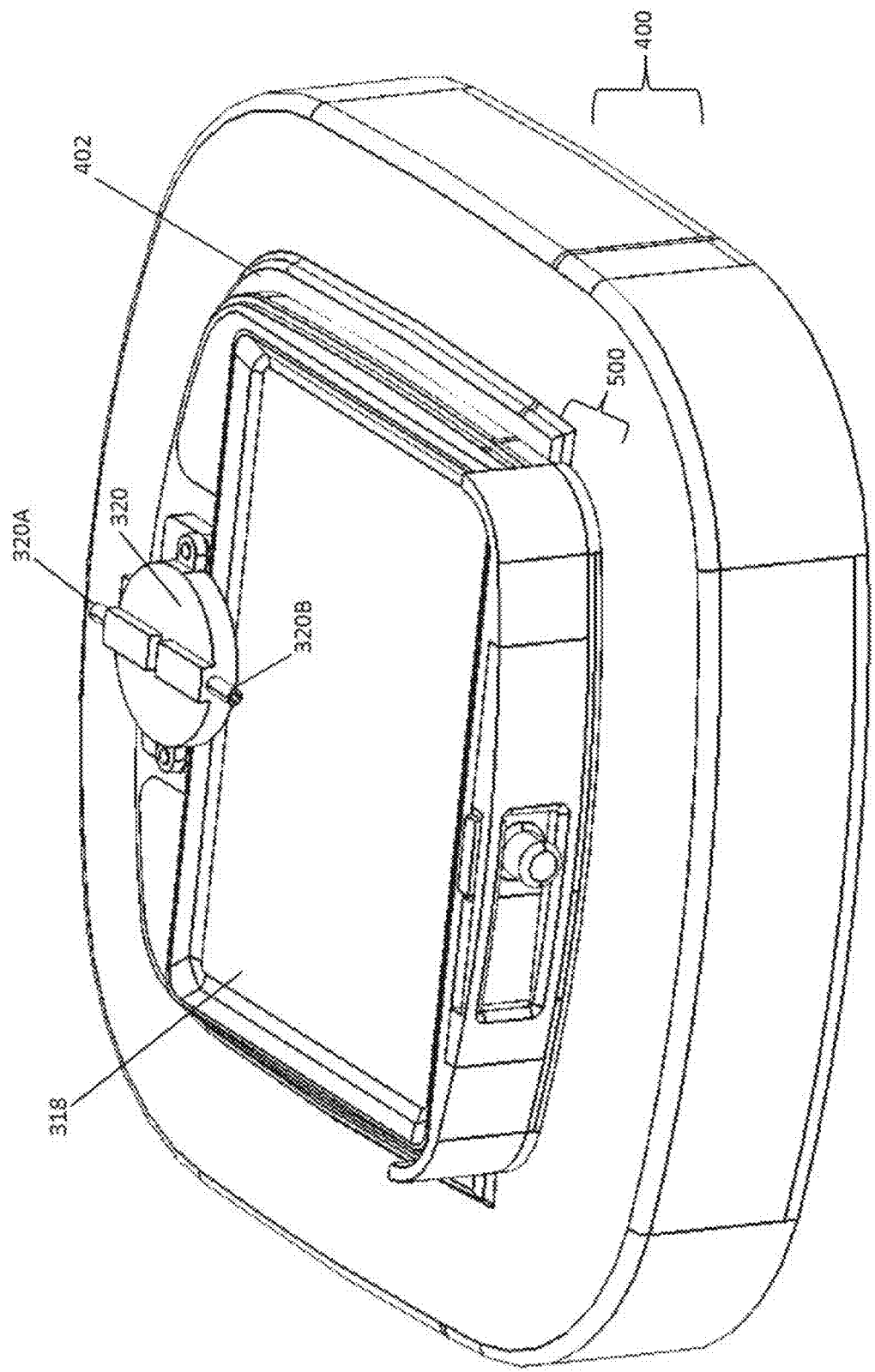
FIG. 5 shows a front perspective view of a portion of a gases humidifier.

FIGS. 4A through 5 show alternative views of portions of the respiratory therapy system 100, where in each instance the flow generator 200 has been removed from the view. As shown, an electrical connector 322 extends from the bottom portion 314 (e.g. from the printed circuit board) of the gases humidifier 300 and is adapted to project through the aperture 308 to interface with a complementary electrical connection region of the flow generator 200. The gases humidifier 300 additionally comprises a metering arrangement/device 320. The metering arrangement 320 comprises an arrangement inlet 320A and an arrangement outlet 320B. As shown the metering arrangement 320 comprises a piezoelectric micropump. The micropump is anchored to a raised portion of the base component 316 (e.g. by screws or pins) that extends through or is accessible through a complementary gap in the bottom portion 314 (e.g. through a gap in the printed circuit board). As can be seen in FIG. 4B, when the gases humidifier 300 is assembled the arrangement inlet 320A of the metering arrangement 320 protrudes through the fluid inlet aperture 302 (defined between the top and bottom portions 310, 314 by a cut-out in the side wall 312). Locating features (e.g. ridges or raised portions) 324, 326 (see FIG. 4C) on the underside of the top portion 310 help to keep the metering arrangement 320 (e.g. the arrangement inlet 320A and arrangement outlet 320B) in a desired orientation. The arrangement inlet 320A can interface with the fluid outlet 406 of the fluid reservoir 400 (through the fluid tubing 410) such that the metering arrangement 320 can transfer fluid from the fluid reservoir 400 to the chamber. Additionally, when the gases humidifier 300 is assembled the arrangement outlet 320B extends into the chamber. The arrangement outlet 320B is positioned above the thermally conductive element 318 such that fluids exiting the arrangement outlet 320B are deposited onto the thermally conductive element 318.

Integrating the metering arrangement 320 into the gases humidifier 300 allows for greater convenience and improved humidification efficiency. In particular, if the metering arrangement 320 is integrated into the chamber, the chance of losing or damaging the metering arrangement 320 is significantly less than if the metering arrangement 320 were positioned outside of the chamber. The aesthetic appeals of the gases humidifier 300 and of the respiratory therapy system 100 are improved when the metering arrangement is integrated into the gases humidifier 300. Additionally, in the illustrated configuration a separate fluid tubing 410 to transfer fluids from the metering arrangement 320 to the chamber is unnecessary, reducing expenses and energy required to transfer the fluid. Heating the metering arrangement 320 by locating it in the chamber such that it is at least indirectly affected by the heat generated by the heater (present on, for example, the bottom portion 314) may improve the efficiency of the metering arrangement 320.

In the illustrated configuration, the micropump of the metering arrangement 320 is configured to transfer fluids from the fluid reservoir 400 or from a separate fluid container to the chamber (e.g. onto the thermally conductive element 318). In other configurations, the micropump may also be configured to run in reverse, e.g. to pump fluid out of the chamber (e.g. from the thermally conductive element 318). Running the micropump in reverse can help to evacuate the chamber if too much water is placed into the chamber. In some configurations, the metering arrangement 320 may be configured to move fluids within the chamber or to move fluids already on the thermally conductive element 318 (e.g. circulation and re-circulation of the fluids). Agitating the fluids may improve the efficiency of humidification.

It should be understood that the metering arrangement 320 is not necessarily limited to comprising a micropump. In other configurations, other displacement pumps, including but not limited to peristaltic pumps, progressive cavity pumps, rotary vane pumps, and Roots-type pumps, may be used to transfer fluid. Additionally, the metering arrangement 320 need not necessarily comprise a pump. For example, if the fluid source (e.g. the fluid reservoir 400 or a separate fluid container) can be suspended above the chamber, the metering arrangement 320 may comprise an electromechanical (e.g. solenoid) valve allowing for fluids positioned above the valve to be controllably deposited into the chamber (e.g. onto the thermally conductive element 318).

In other configurations, the metering arrangement 320 need not necessarily be screwed or bolted onto the base component 316. For example, the metering arrangement 320 may be integrally formed with or share a joint housing together with the base component 316. In some configurations, the metering arrangement may be adhered to the base component 316 or to another component of the respiratory therapy system 100 (including but not limited to the flow generator 200, the gases humidifier 300, or the fluid reservoir 400), or retained using a variety of mechanical fastening arrangements including but not limited to hook-and-loop connections or latch/catch arrangements. In some configurations, the locating features 324, 326 on the underside of the top portion 310 may not be present.

FIGS. 6A through 6D show exploded and perspective views of portions of the gases humidifier 300 together with the locking engagement arrangement 500, in which each instance the top portion 310 has been removed from the view. In the illustrated configuration, the locking engagement arrangement 500 comprises a back panel 502. The back panel 502 comprises a frame that extends along a side of the base component 316. The frame comprises a recessed region 502A in which a window panel 504 rests. Raised portions 502B, 502C of the frame interface with complementary recesses 504B, 504C on a rear portion of the window panel 504. The window panel 504 defines a window 504A in which an engagement structure 506 rests. The engagement structure 506 comprises a substantially rectangular panel comprising a protrusion or knob 506A and projections 506B, 506C that extend axially from the panel in directions substantially perpendicular to the protrusion 506A. When the locking engagement arrangement 500 is assembled, a slot is defined between the back panel 502 and the window panel 504 in which the engagement structure 506 can be slideably positioned. The base component 316 comprises a recessed track 508 in which the bottom projection 506C can move.

Figure 6A:
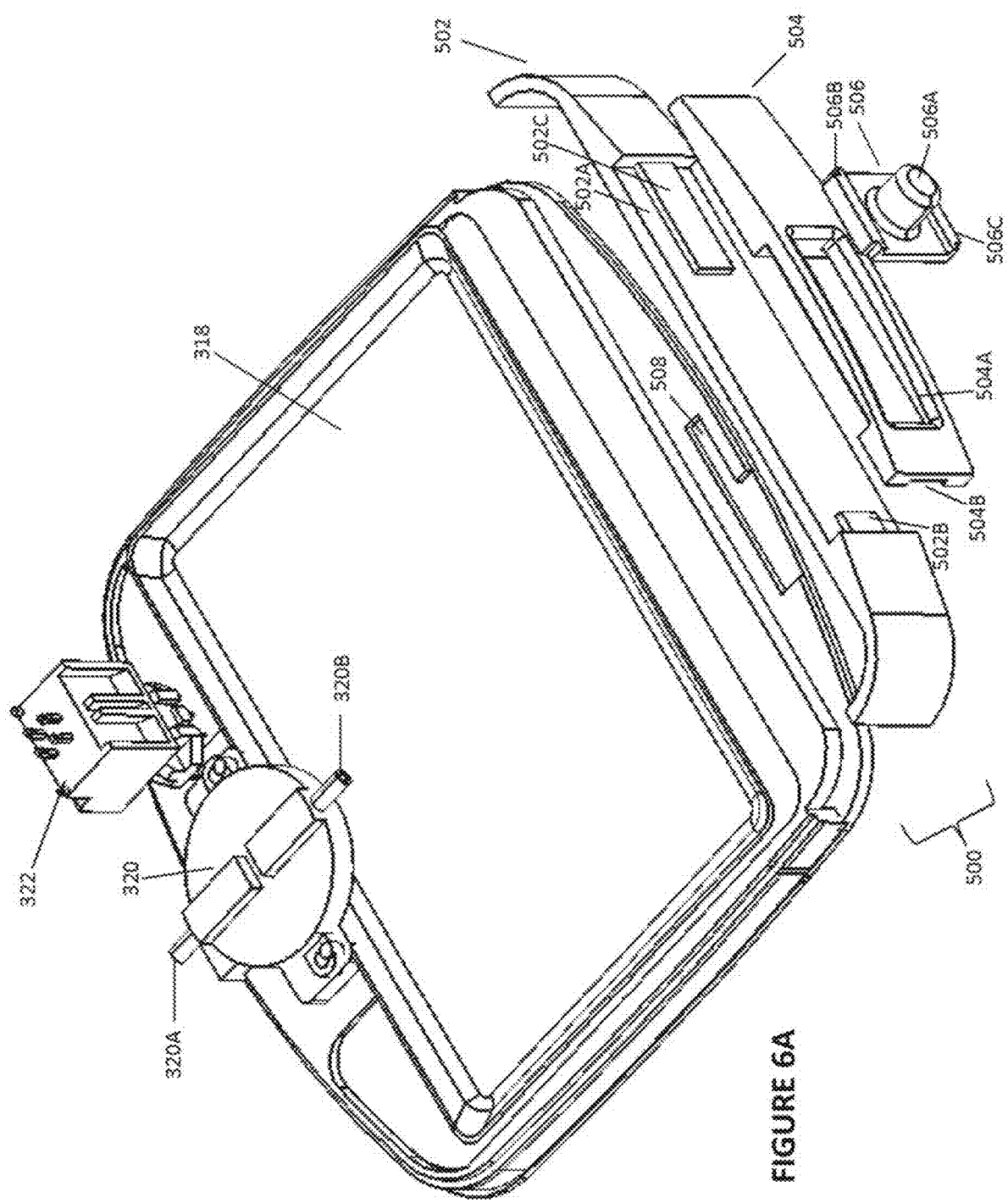
FIG. 6A shows an exploded elevated front perspective view of a portion of a gases humidifier.
Figure 6B:
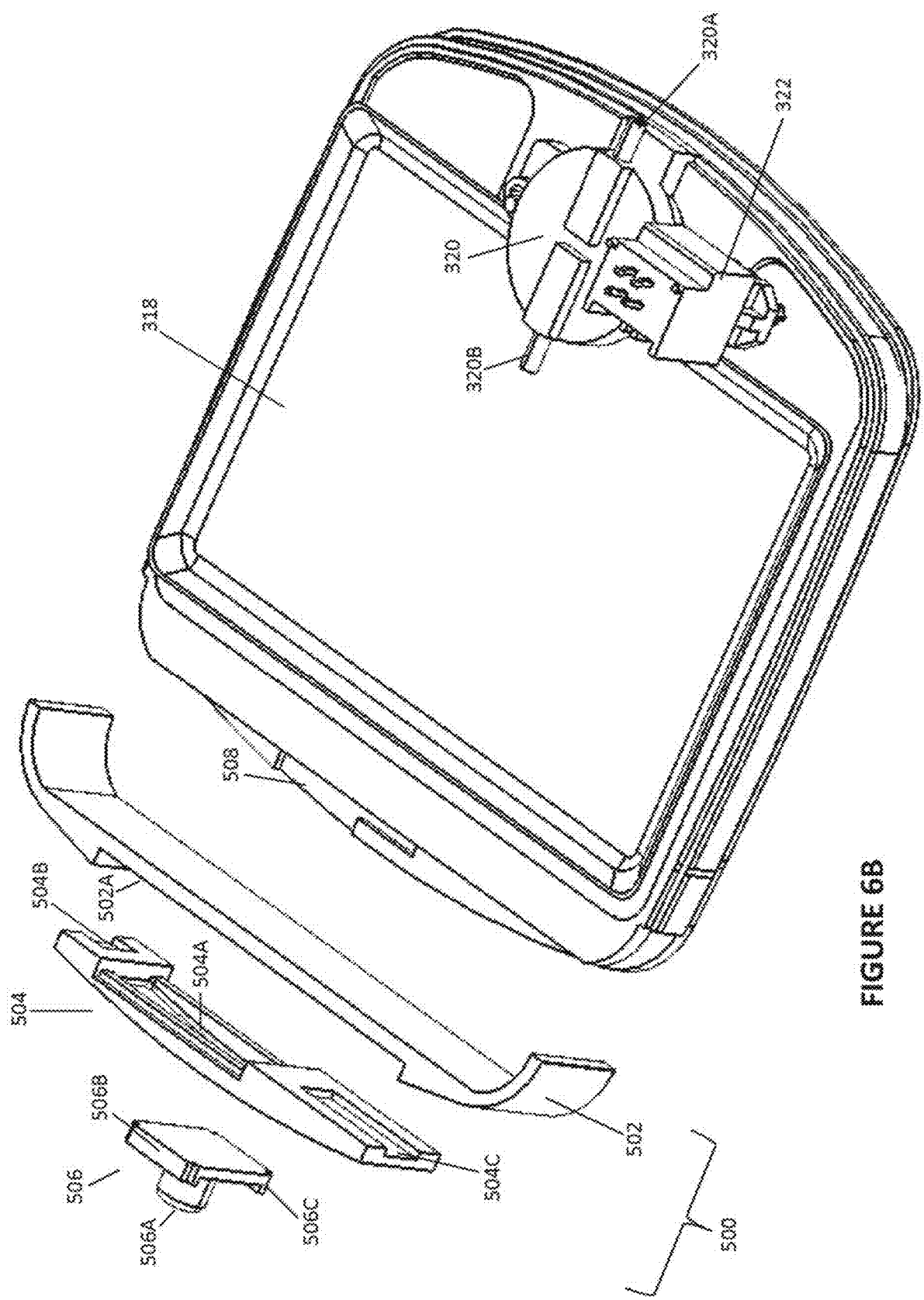
FIG. 6B shows an exploded elevated perspective view of a portion of a gases humidifier.
Figure 6C:
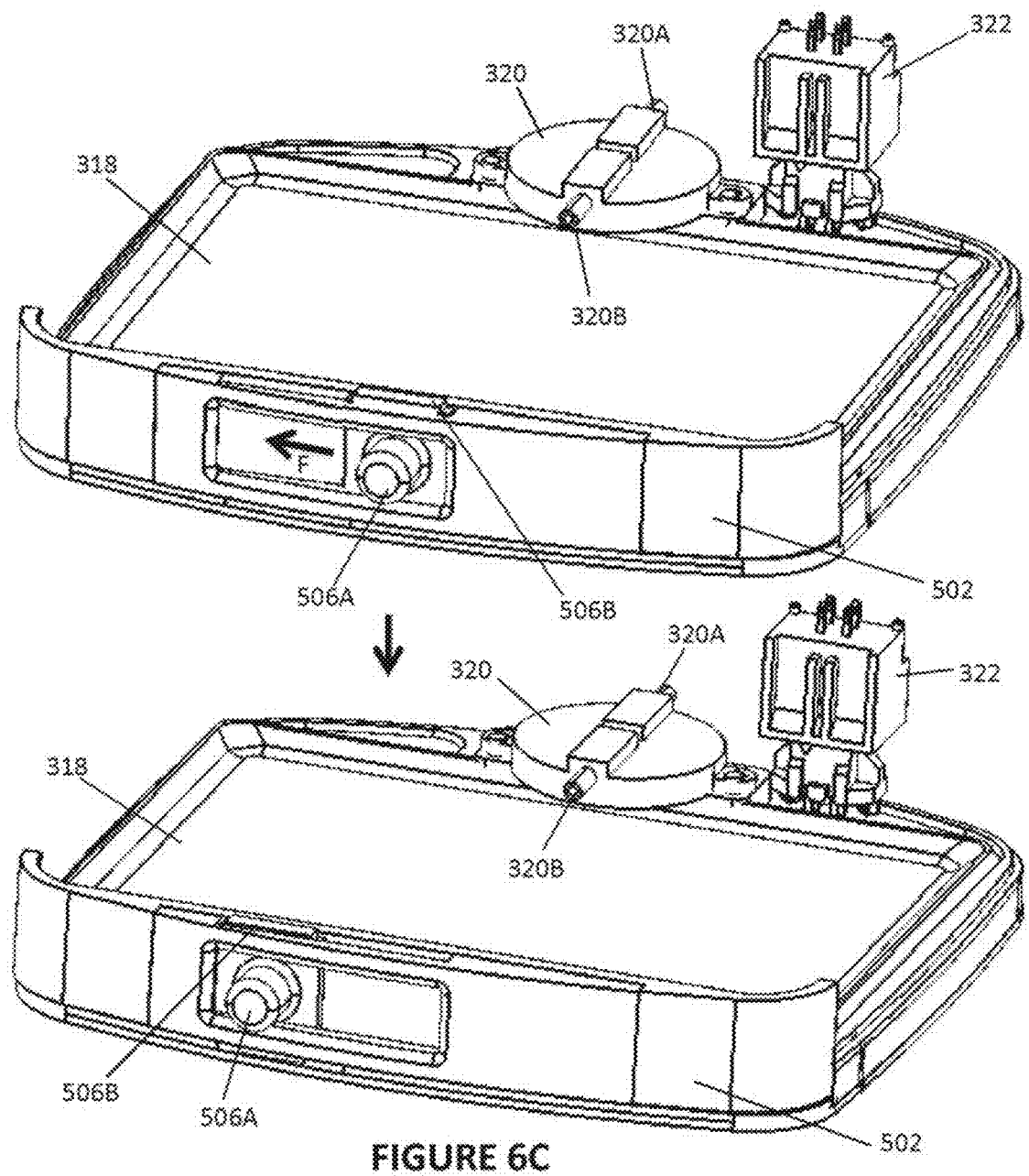
FIG. 6C shows an elevated front perspective view of a portion of a gases humidifier.
Figure 6D:
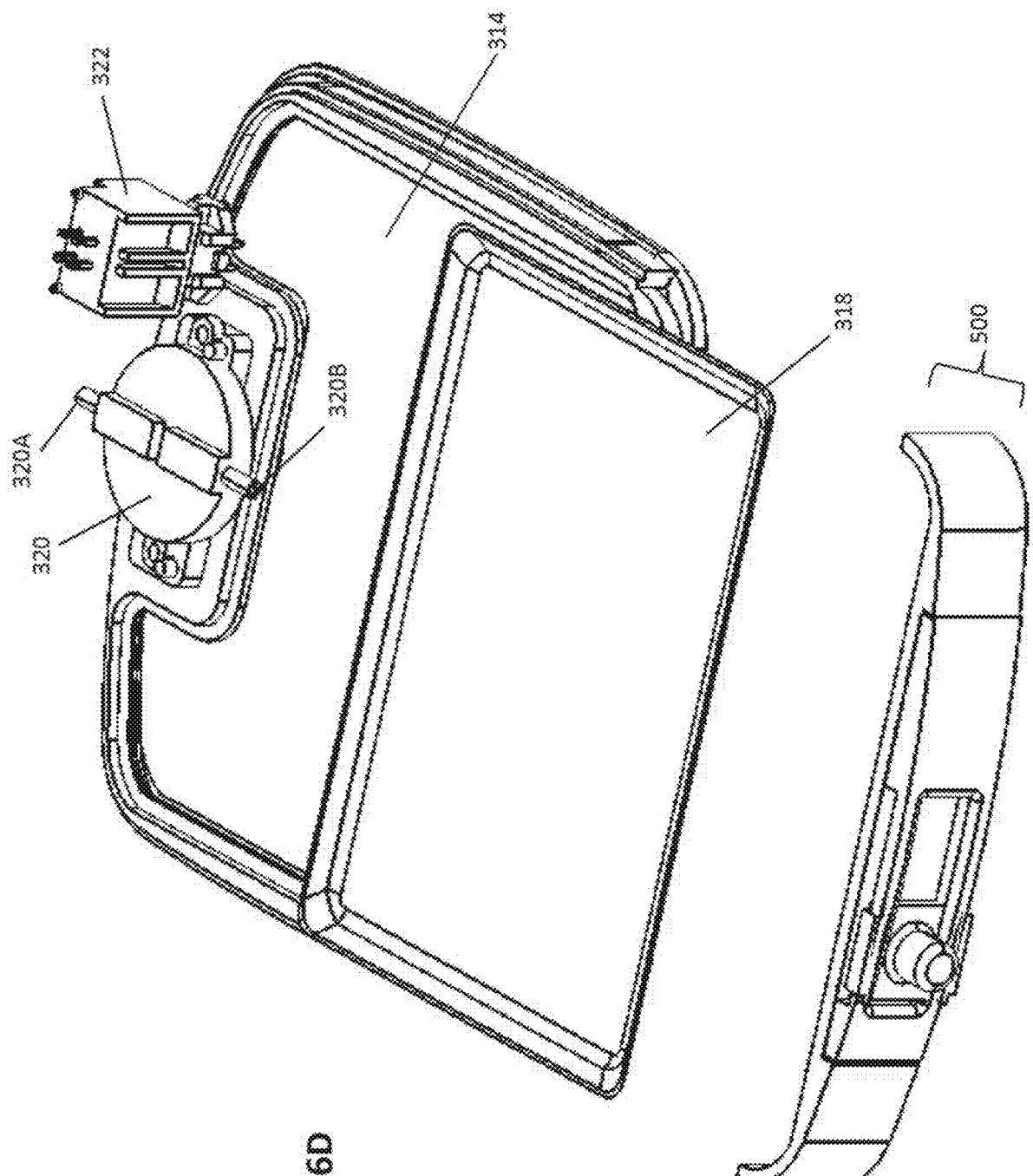
FIG. 6D shows an elevated front perspective view of a portion of a gases humidifier.

FIGS. 6C-6D demonstrate the function of the locking engagement arrangement 500. In a locked position, the protrusion 506A of the engagement structure 506 is positioned (e.g. on the right as viewed in the top drawing of FIG. 6C) such that movement of the locking engagement arrangement 500 away from the gases humidifier 300 is prevented. The bayonet-style shape of the recessed track 508 (e.g. the right portion as viewed in FIG. 6A) serves to trap the bottom projection 506C. When the protrusion 506A is moved (e.g. manually with a force F as shown using the black arrow present in the top drawing of FIG. 6C) towards an open position (e.g. towards the left as viewed in the bottom drawing of FIG. 6C), the bottom projection 506C is urged towards an open portion of the recessed track (e.g. the left portion as viewed in FIG. 6A). When in the open position, and as seen in FIG. 6D, the locking engagement arrangement 500 can be removed to allow access to the chamber of the gases humidifier 300. As such, when the locking engagement arrangement 500 is in the open position, the thermally conductive element 318 may be removed and replaced. Allowing for removal and replacement of the thermally conductive element 318 reduces the need for cleaning and improves the sterility of the gases humidifier 300. Alternatively, if the thermally conductive element 318 is intended to be used permanently or for a significant period of time over the lifetime of the gases humidifier 300, allowing for removal of the thermally conductive element 318 allows for easier cleaning. When the locking engagement arrangement 500 is in the closed position, the thermally conductive element 318 may be locked in place. The locking engagement arrangement 500 also seals the chamber to prevent gases passing through the gases humidifier 300 from passing directly into the ambient atmosphere.

In other configurations, the top and/or bottom projections 506B, 506C may alternatively or additionally engage with complementary recesses or tracks present on the top and/or bottom portions 310, 314 (e.g. present on the underside of the top portion 310 and/or on the top of the bottom portion 314). In some configurations, a part of the locking engagement arrangement 500 or a part of the gases humidifier 300, including but not limited to a surface of the back panel 502 facing the chamber and a wall of the gases humidifier 300 defining the chamber, may comprise a sealing structure adapted to seal the chamber when the locking engagement arrangement is fixed to the gases humidifier 300. The sealing structure may comprise a number of elements including but not limited to resilient silicone flanges or beads. In other configurations, other mechanical fastening arrangements for use with the locking engagement arrangement 500 to retain the thermally conductive element 318 in the chamber may be used, including but not limited to latch/catch arrangements, snap-fit arrangements or hinged door arrangements. Instead of sliding the protrusion 506A back in forth to open or close the locking engagement arrangement 500, in some configurations the locking engagement arrangement 500 may simply go from closed to open positions after the application of a predetermined amount of force urging the locking engagement arrangement 500 away from the gases humidifier 300. In some such configurations, the locking engagement arrangement 500 may comprise a handle extending outwardly from the back panel 502 to allow a user to apply force to the locking engagement arrangement 500.

In other configurations, a springing mechanism may be used to apply a biasing force to the thermally conductive element 318. The springing mechanism can include a number of components, including but not limited to helical wire springs, flat springs, or resilient materials. The springing mechanism may be secured to the side wall opposite the side of the gases humidifier 300 at which the thermally conductive element 318 is introduced to the chamber. As the thermally conductive element 318 is pushed into the chamber, the springing mechanism may in turn bias the thermally conductive element 318. Subsequently, when the locking engagement arrangement 500 is attached to the gases humidifier 300 and switched to the locked position, the springing mechanism may help to retain the thermally conductive element 318 in the chamber. When the locking engagement arrangement 500 is switched to the open position, force stored in the springing mechanism may be used to at least in part eject the thermally conductive element 318 from the chamber.

In still other configurations, the locking engagement arrangement 500 may not be present, and the thermally conductive element 318 may be permanently positioned within the chamber of the gases humidifier 300. In still other configurations, other components of the gases humidifier 300 ('humidification elements'), including but not limited to the heater positioned on the bottom portion 314, may be removed when the locking engagement arrangement 500 is in the open position. In still other configurations, the thermally conductive element 318 may be integrally moulded or in the form of a single continuous component together with the locking engagement arrangement 500. Removing the locking engagement arrangement 500 from the gases humidifier 300 may have the effect of simultaneously removing the thermally conductive element 318 from the chamber.

In some configurations, the flow generator 200 may comprise a lid or a cap adapted to sealingly close the aperture or apertures in the housing of the flow generator 200 that can be pneumatically coupled to the gases humidifier inlet 304 and gases humidifier outlet 306 openings of the gases humidifier 300. The lid may be physically separate from the flow generator 200 and may be removably connectable to the flow generator 200 (via any number of arrangements, including but not limited to frictional, snap-fit or bayonet-style connections). In other configurations, the lid may be permanently fixed to the flow generator 200 and moveable to occlude or expose the aperture or apertures. For example, the lid may be slideably coupled to the flow generator 200. The lid may be slid in a first direction to occlude the aperture or apertures and may be slid in a second direction to expose the aperture or apertures. In some configurations, multiple lids may be used.

In some configurations, a fluid filter may be placed in or near the fluid tubing 410, metering arrangement 320, gases humidifier 300 and/or fluid reservoir 400. The fluid filter may be configured to remove contaminants from the fluids metered by the metering arrangement 320 before the fluids enter the chamber. The fluid filter may be anti-pathogenic (e.g. antibacterial, antiviral, antifungal, etc). For example, the fluid filter may comprise organic anti-bacterial compounds or particulate silver.

In some configurations, some or all of the gases humidifier 300 may be joined to a housing adapted to cover all components of the gases humidifier 300 except for the gases humidifier inlet 304 opening, the gases humidifier outlet 306 opening, the locking engagement arrangement 500 (which is removable to allow access to the chamber and the thermally conductive element 318), and an electrical connector (for power and/or data). The housing could be designed such that the gases humidifier 300 may be used with a multitude of different flow therapy systems. For example, the housing may have movable panels that may transpose the position of the humidifier inlet 304 opening and/or the position of the humidifier outlet 306 opening. In some cases the electrical connector may transposable on the exterior of the housing (using, for example, a flexible or movable electrical harness). In other such configurations, the locking engagement arrangement 500 may not be present and the thermally conductive element 318 may be permanently set in the chamber.

Operation of the device will now be described. The reservoir 400 is filled with fluid and the apparatus assembled. A breathing conduit 112 and patient interface are connected to the outlet 204. The respiratory therapy system 100 can then be switched on and operated using the user interface in the usual manner. Under control by the controller 110, the flow generator 200 (by way of the blower) will create a flow of gases in the usual manner for a respiratory therapy system and the gases will flow through the humidifier. The controller operates the pump 320 to provide a metering arrangement to transfer water from the water reservoir to the conductive element 318. This creates a thin layer of water over some or all of the element. The controller operates the heater 314 to create a heat which is then transferred through the element 318 to heat the thin layer of water. Gases from the flow generator 200 passes over the water, and absorbs moisture, thus humidifying the gases. The gases then flow out for delivery to the patient through a breathing conduit 112 and patient interface 116 in the usual manner.

FIGS. 7A to 15 show another non-limiting exemplary embodiment of a respiratory therapy system 100. A brief overview of the embodiment will be described with reference to FIGS. 7A, 7B, and various components will later be described in more detail with reference to all FIGS. 7B to 13.

Figure 7A:
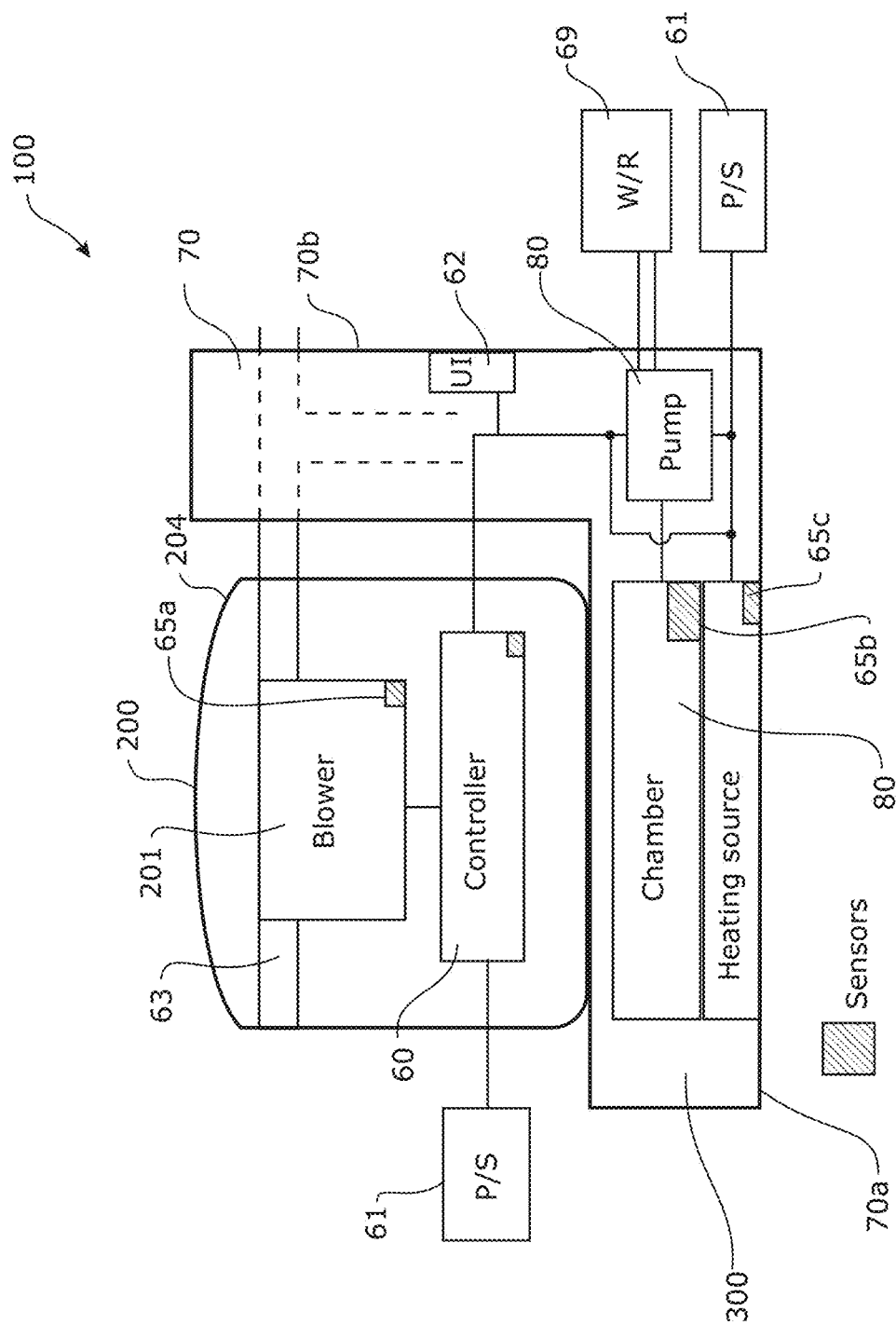
FIGS. 7A, 7B shows another embodiment of the respiratory therapy system in assembled form.
Figure 7B:
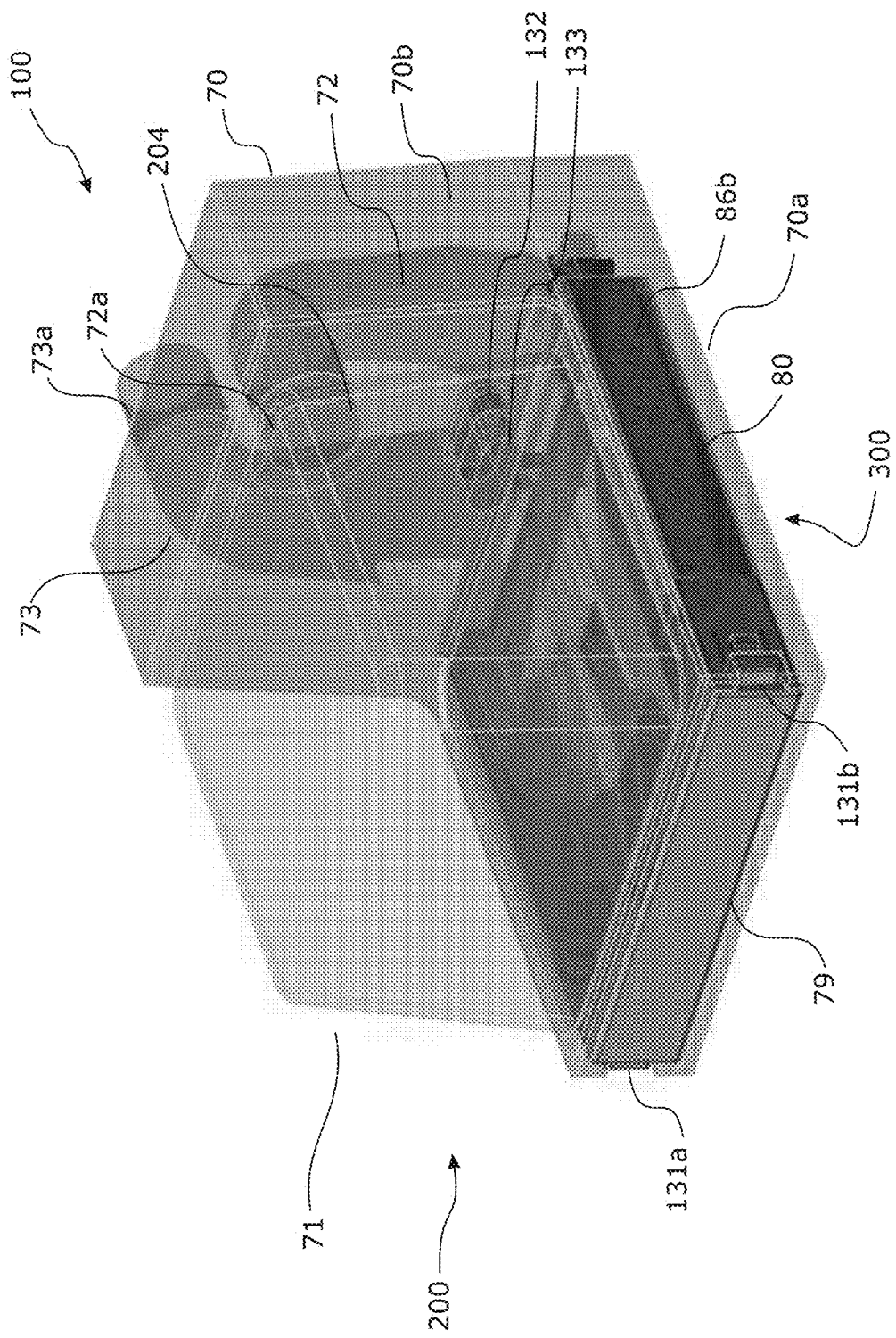
Figure 8:
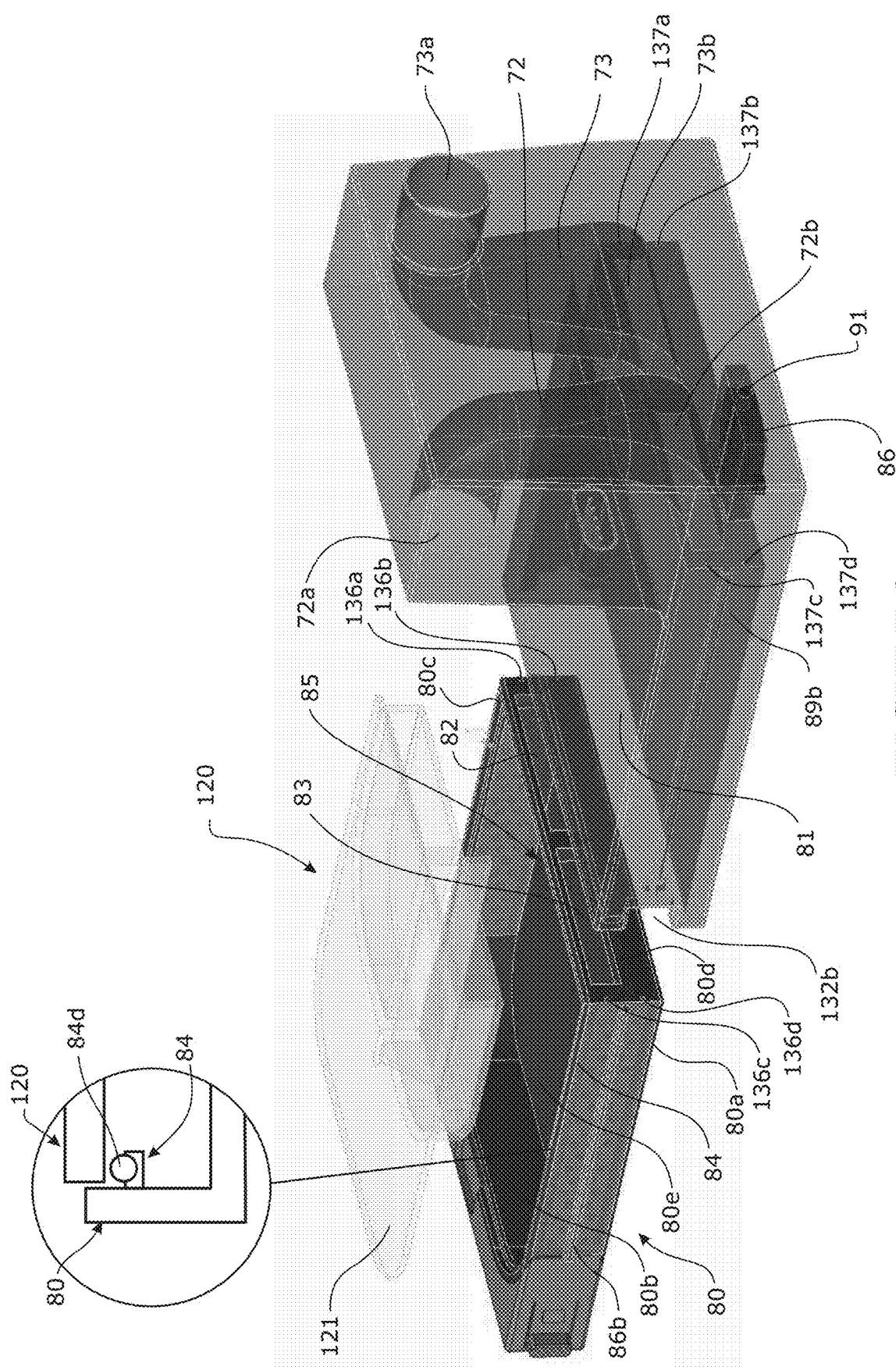
FIG. 8 shows the respiratory therapy system with the water chamber cartridge in exploded form.

FIG. 7A shows the system in diagrammatic form, and FIG. 7B shows one physical form of the system. Some of the components are not shown in both Figures for reasons of clarity, but it will be appreciated that the embodiment comprises the components of both Figures, where appropriate. As shown, the respiratory therapy system 100 comprises a main housing 70, a flow generator 200, and a gases humidifier 300. The main housing 70 comprises a base portion 70a that contains the humidifier 300, and has a top face 81 (see e.g. FIGS. 8, 9a, 9b, 10) for supporting/receiving the flow generator 200. The main housing 70 also has an upright/back portion 70b, which comprises a respiratory therapy system outlet conduit 73, a humidifier inlet conduit 72, connector 132, and other components of the respiratory therapy system. A metering device 86 is also provided in the system 100 for delivering fluid to the humidifier.

The flow generator, base 70a and/or upright 70b housing portions and/or humidifier 300 can also contain the other components of a respiratory therapy system, such as a controller 60, power source 61, sensors 65a-65c and user interface 62. The power source might also be external, or a combination of external and internal, and there might be more than one power source. The system 100 preferably has one or more sensors (e.g. 65a, 65b, 65c shown in FIG. 7a) for measuring temperature, humidity, flow, pressure and/or other parameters (ambient or otherwise, relative or absolute) coupled to the controller for aiding operation of the system 100. The sensors could, for example, be positioned with/coupled to the blower, cartridge chamber, gas flow paths and/or heating element—as well as other locations. The sensors 65a, 65b, 65c are coupled to the controller 60. The controller 60 (coupled to and using output from the sensors as required) can control the blower 201, humidifier 300, user interface 62, metering arrangement/device (e.g. pump) 86 and/or other components or operations of the system 100 in a manner known to those skilled in the art. Various configurations, placements and interconnections of the controller, power source, sensors, metering device and user interface will be described herein by way of example, but these should not be considered limiting. Those skilled in the art will understand that other configurations, placements and interconnections of these and other components are possible.

The various components of the respiratory therapy system will now be described in further detail.

Figure 15:
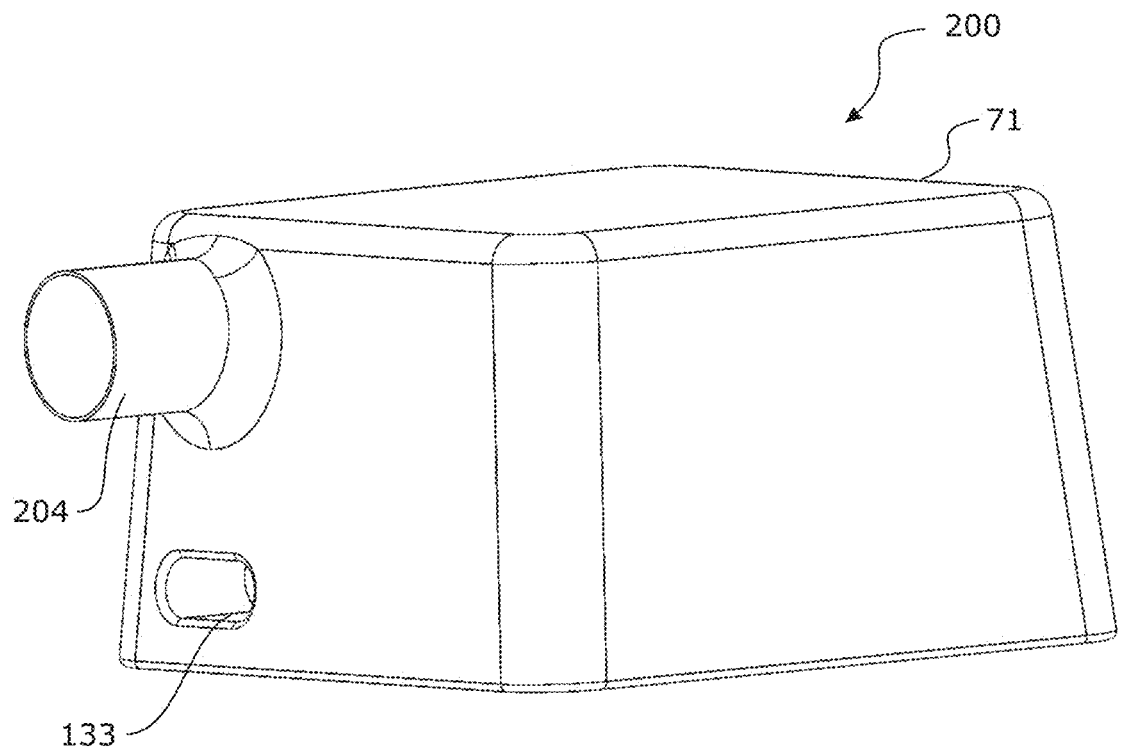
FIG. 15 shows a flow generator of the respiratory therapy system.

The flow generator (shown in isolation in FIG. 15) has a housing 71 and inside the housing there is a blower apparatus 201 (such as a PAP device). An example is shown in FIGS. 1 and 7A. The blower apparatus 201 may include, for example, one of the blower apparatus described in WO2013/009193, the contents of which are hereby incorporated by reference in its entirety. The flow generator 200 comprises a gases inlet 63 (shown in FIG. 7a) and a gases outlet 204. The flow generator optionally contains one or more temperature, humidity, flow and/or pressure sensors (shown as 65a in FIG. 7a) on the inlet, outlet, in any suitable gases flow path and/or any at other suitable location. The blower apparatus 201 in use draws gases through the inlet 63 and delivers a flow of gases through the gases outlet 204 via a gases conduit (for example, a gases conduit 72 described elsewhere in this disclosure with reference to the Figures) towards the humidifier 300. Preferably the gases inlet 63 and gases outlet 204 form part of and/or extend through the flow generator housing 71 (as seen in FIG. 15, for example).

The flow generator also preferably comprises the controller 60, which is coupled to the sensors 65a to 65c (arranged on the blower and/or elsewhere in the system 100) and is also coupled to and operates the blower 201, humidifier 300, pump 86 (to be described later), user interface 62 and/or other operations and/or components of the system 100. The controller is coupled to an external (or alternatively internal) power source 61, which may also directly or indirectly power the blower 201 and/or other components of the system. The controller 60 alternatively could be disposed in other parts of the system 100. The housing 71 of the flow generator 201 comprises a connector 133 for coupling to a corresponding connector 132 on the main housing 70. For example, the connector might be a socket connector for coupling to pins on the corresponding connector on the main housing. The connector 133 is for transferring power and/or data/signals (from the power source and/or controller and/or sensors) between the flow generator 201 and the main housing 70, and for transfer to other parts of the system. For example power can be transferred via the connector 133 to the flow generator from the main housing, or vice versa depending on the position of the power source. Similarly, signals from the controller can be transferred to other parts of the system via the connector 133, and/or signals from sensors 65a to 65c from other parts of the system can be transferred to the controller via the connector 133. Other alternatives of power and/or signal flow between various components could also be envisaged by those skilled in the art.

Preferably, the base portion 70a of the respiratory system main housing 70 and/or the base of the blower housing 71 are configured to enable the blower housing 201 to be received on and removed from the base portion 70a by sliding the blower housing 71 onto the base portion 70a/top surface 81 from the front of the respiratory therapy system. There could be rail/guides and/or other detailing to achieve this. There is also preferably a locking mechanism to lock the flow generator 200 to the base 81. It will be appreciated by those skilled in the art that other forms of attachment and removal of the blower from the housing could be envisaged.

The gases humidifier 300 is a modular construction and is detachably fixable (in part or in entirety) to the respiratory therapy system 100, and preferably the base portion 70a thereof. The humidifier 300 comprises a water chamber cartridge 80, with four sides 80a-80d, a bottom 80e and an open top defining a chamber 85 for fluid (e.g. water). The back wall 80d comprises two openings 82, 83. The first opening 82 is a gases inlet to the water chamber cartridge for receiving gases flow from the flow generator 200. The second opening 83 is a humidified gases outlet from the water chamber cartridge for emitting humidified gases flow from the chamber destined for patient outlet 73a. The base 80e of the water chamber cartridge comprises a heat conducting plate, such as an aluminium plate, which may form part of or all of the base of the water chamber cartridge 80. The base can comprise microstructures and/or a hydrophilic coating to promote a thin layer of water to spread.

The cartridge also comprises a lid 120 (shown in isolation in FIGS. 12a—top view, 12b—bottom view) with a plate 121 that sits over and rests atop the side walls 80a-80d. A ridge/recess 84 extends around the top of the side walls 80a-80d of the chamber 80 which corresponds to a similarly shaped perimeter of the lid 121 to enable engagement and sealing of the lid 121 and the side walls 80a-80d to create a sealed (chamber) 85 in the water chamber cartridge 80. The lid is kept closed tight using the geometry of the housing (compression). As shown in the diagrammatic insert in FIG. 8, there is preferably a seal 84a (e.g. rubber or silicon seal) also to provide a water and air seal between the lid and side walls. The seal could alternatively be on the cartridge exterior. The seal can help reduce leakage if the humidifier 300 is tilted. The lid 121 can be locked onto the body of the water chamber cartridge via a latch, spring or similar, if required. The lid also comprises a baffle 127, comprising a bottom plate 122 that is suspended from the bottom side of the lid plate 121 by a side wall(s) 123. The baffle comprises a central dividing wall 124 extending from the lid plate 121 that divides the baffle into two (preferably oblong/rectangular) sections with openings 125a, 126a that correspond in position and shape to the inlet 82 and outlet 83 openings of the water chamber cartridge (which are preferably also oblong/rectangular). The bottom plate 122 also comprises openings 125b, 126b either side of the dividing wall 124. Extending from the bottom plate and part of the top plate is a wall 128 forming a baffle/fin, with a truncated (preferably angled) end.

When the plate 121 of the lid 120 is positioned in place on the side walls 80a-80d, the baffle 127 is suspended down off the lid plate such that the apertures 125a, 126a align with the apertures 82, 83 in the back wall 80d of the water chamber cartridge 80 and the baffle wall 128 forms a barrier to section off part of the chamber cartridge region 85. This forms a gases flow path (show as arrows labelled "airflow") into the inlet aperture 125a, down through the aperture 125b, along the baffle 128 in the first section of the chamber around the truncated end into the second section of the chamber, up through the aperture 126b, along the baffle section and through the outlet 126a. As the gases travels from the aperture 125b to aperture 126b, it contacts heated water in the chamber and becomes humidified.

The lid and in particular the baffle 127 and bottom plate 122 with airflow openings 125b, 126b near the centre of the lid/chamber reduce the chances spillage of water out of the chamber when tilted, for example when tilted at angles up to about <=20 degrees. This reduces the chance that water will back flow through the openings 82, 83 into the flow generator, main housing and/or other parts of the system if the chamber is tilted towards those openings. This is because the openings 125b, 126b are positioned so that during such tilting, the openings are raised above the water level in the chamber. For example, the openings 125b, 125b can be placed as centrally as possible to reduce backflow risk irrespective of which orientation the humidifier is tilted. Also, the fin 128 is truncated to a length so that the gases flow path is not blocked when the chamber is tilted away from the openings 82, 83. There is sufficient gap between the end of the fin 128 and the chamber wall so that the water level does not block gases flow if the chamber, humidifier or entire system is tilted. A further mitigation for this is to have openings at either end of the chamber. Baffles or other geometry are arranged to move air around as much of chamber volume as possible.

Figure 18:
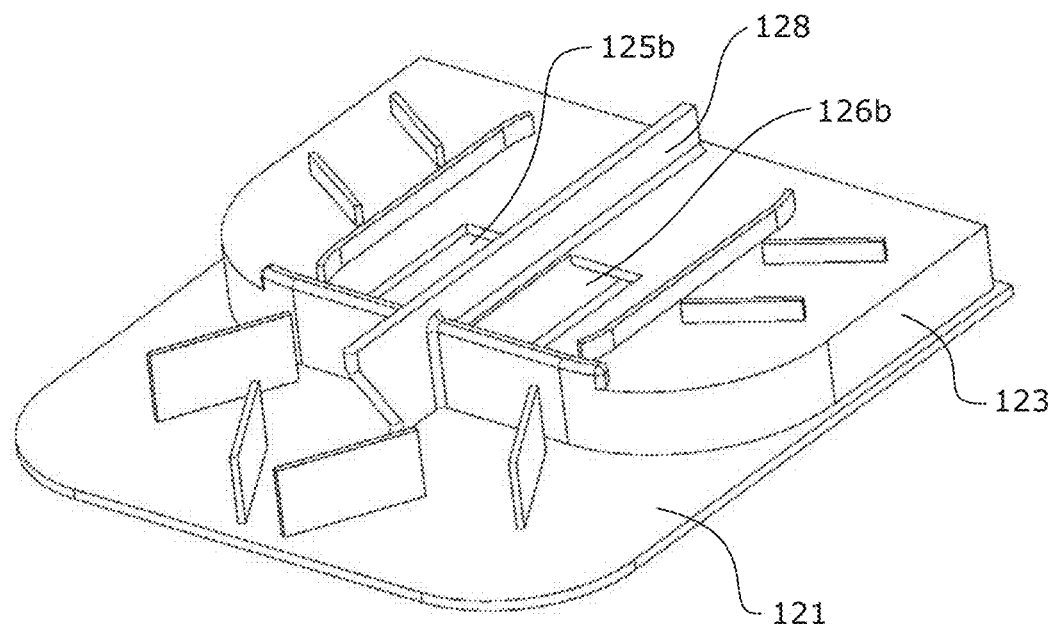
Figure 19:
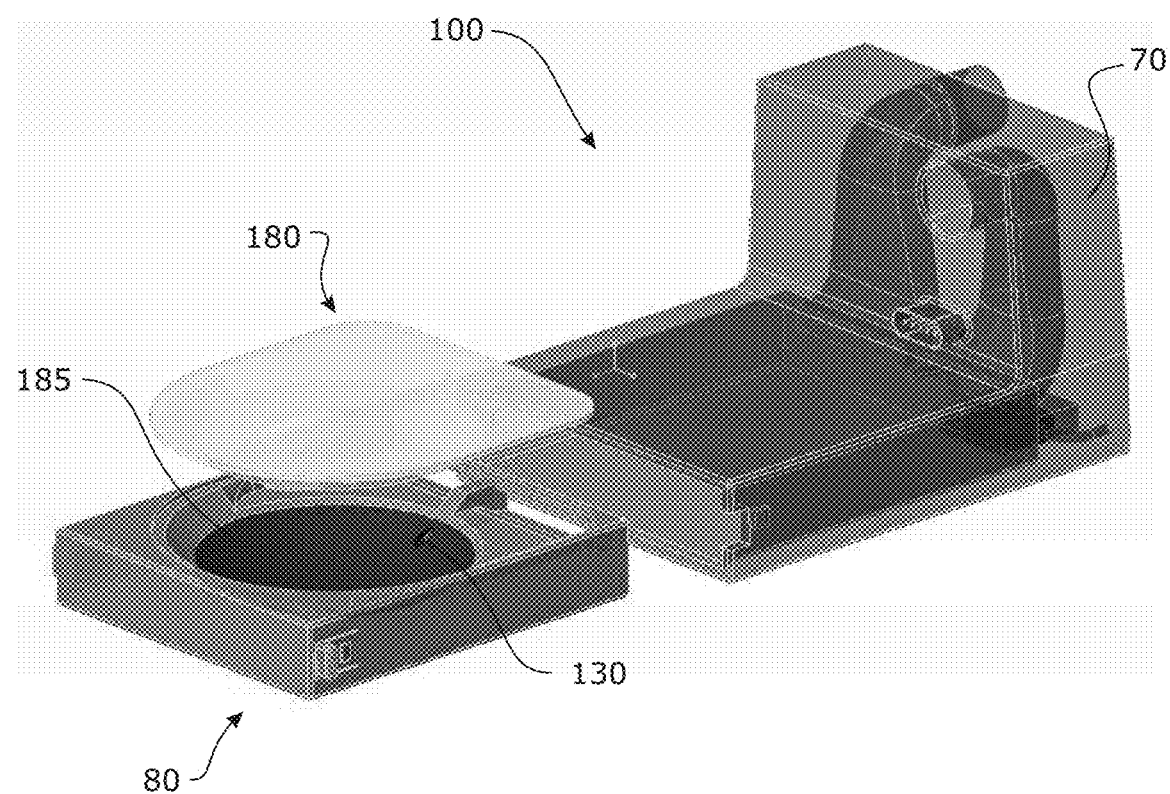
FIGS. 19 to 22 show an alternative water chamber cartridge with a bowl.
Figure 20:
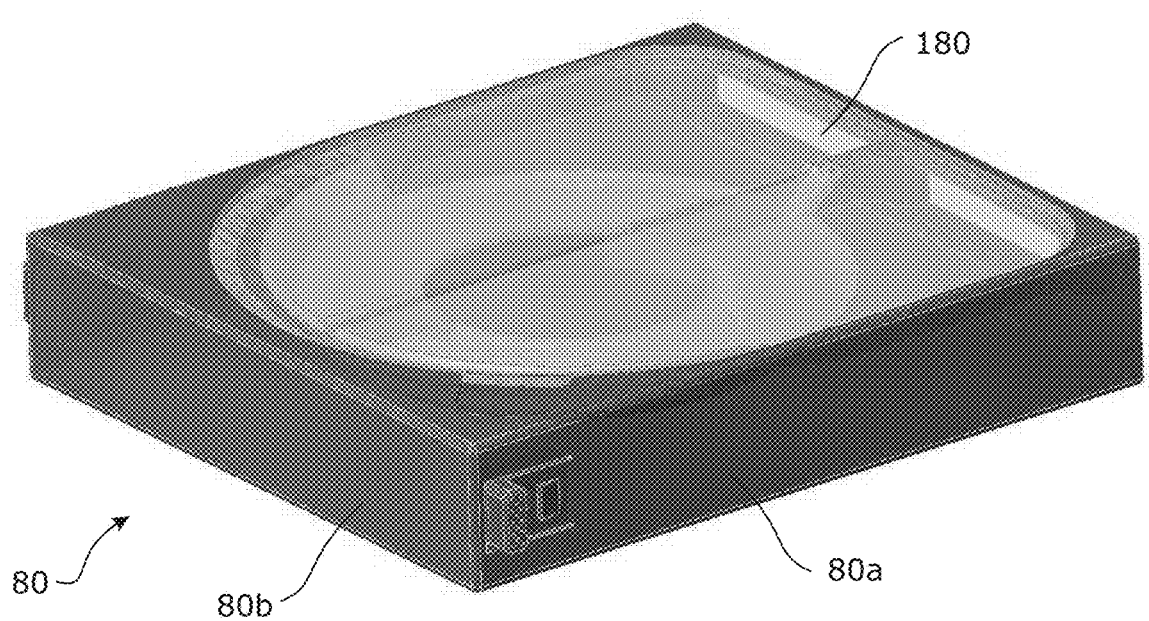
Figure 21:
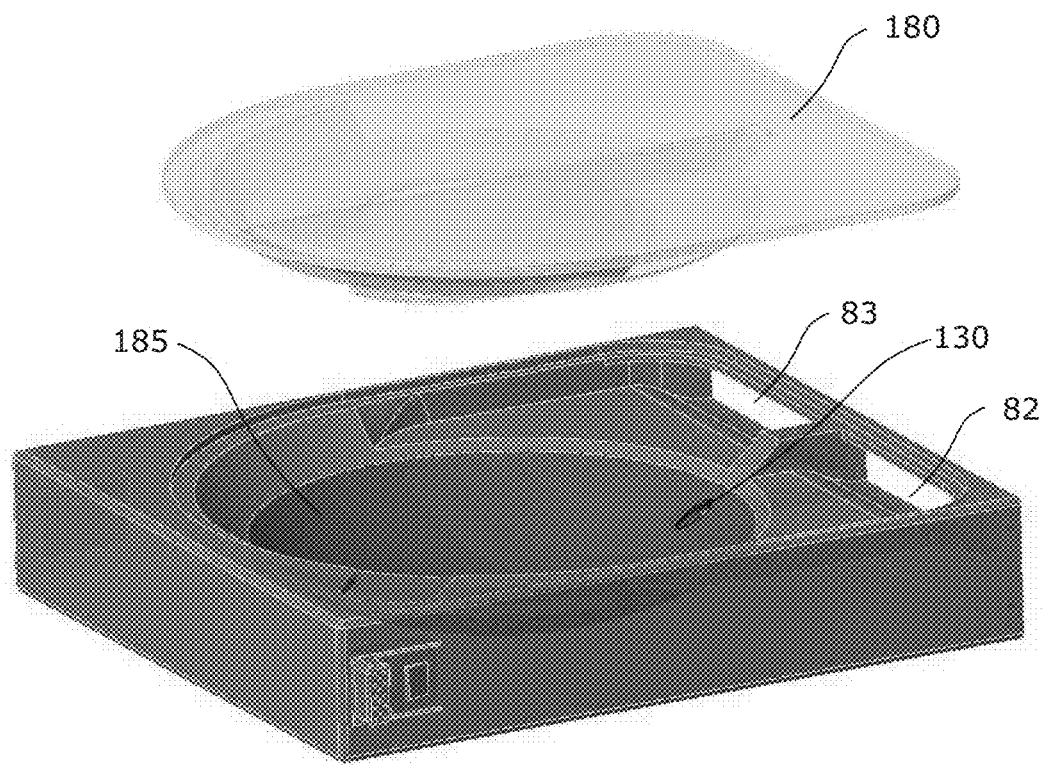
Figure 22:
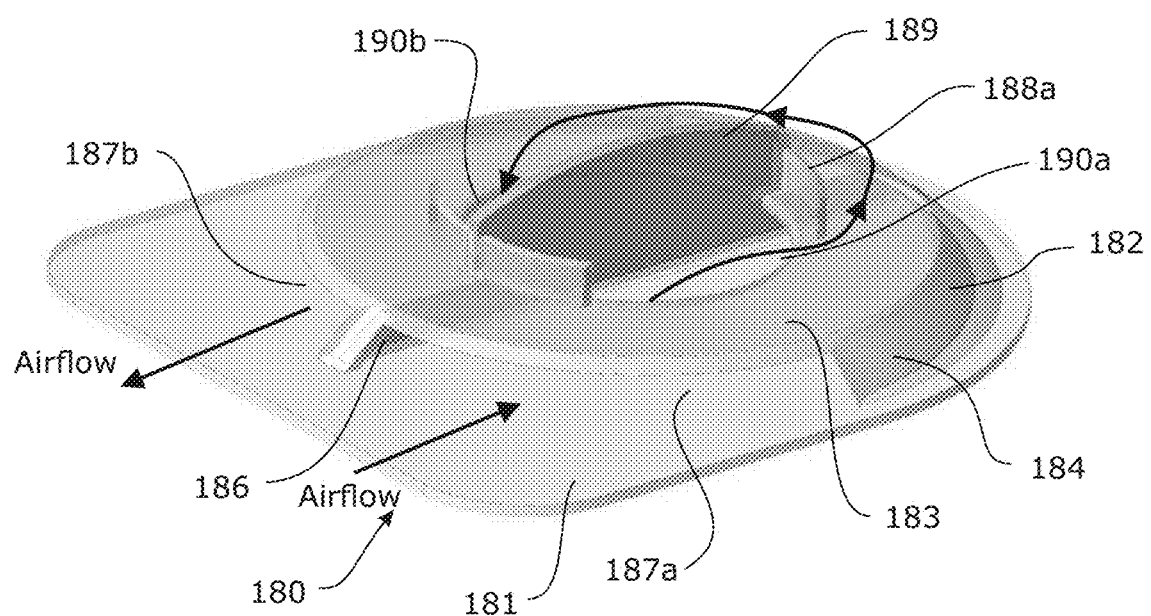

FIG. 18 shows an alternative bottom side of the lid 120, wherein a range of fins/baffles are formed as walls on the bottom of the bottom plate and top plate. These increase the air flow path length, which enables more uptake of moisture by the gas flow.

The back wall 80d of the water chamber cartridge 80 has a fluid (e.g. water) inlet aperture/opening 130 (see FIG. 13), preferably a circular opening, for coupling to the pump 86 (to be described later) to receive humidifying fluid (e.g. water) into the chamber 85. The water chamber cartridge 80 may have (optionally) a detachable front fascia 79, which can clip onto the side walls 80a, 80c. The fascia may optionally be considered part of the water chamber cartridge 80. The fascia alternatively can be fixed or formed integrally with the water chamber cartridge. The fascia has a rebate 78 to assist in removing the lid. Removing the lid allows for access to the chamber for cleaning, emptying etc.

The base portion 70a of the main housing 70 comprises a slot 88 commensurable in size and shape for receiving the water chamber cartridge 80. The slot forms a docking station for the cartridge. Each side wall 88a, 88b of the slot comprises a locator extrusion or other guide 89a, 89b, (such as a rail channel, or other detailing) and there is a corresponding guide 86a, 86b, such as a rail or other detailing, on each side of the water chamber cartridge 80. The water chamber cartridge can be inserted into and removed from the slot 88 by engaging the rails 86a, 86b and the corresponding rail channels 89a, 89b and sliding the cartridge into and out of the slot 88. Pinch clips/latches 131a, 131b on each side of the water chamber cartridge lock it into position by engaging in corresponding rebates 132a, 132b in the base portion 70a of the main housing 70.

Figure 10:
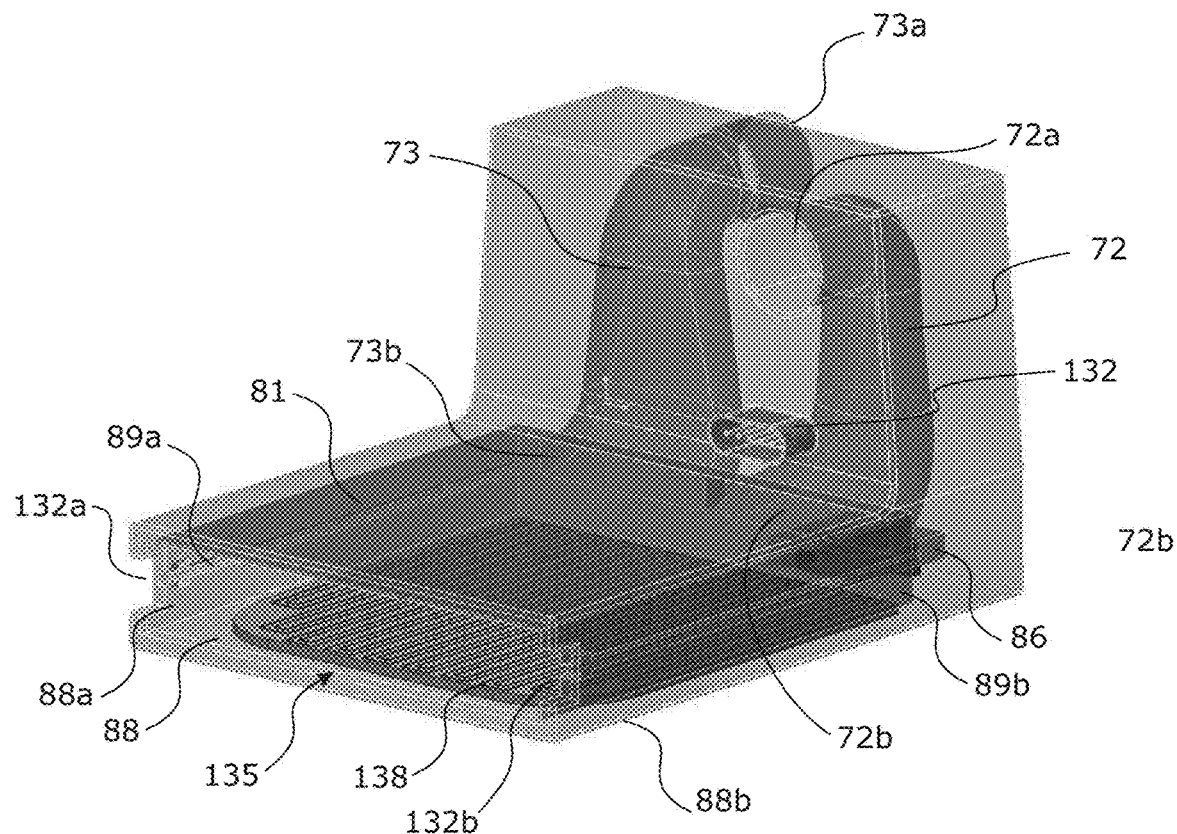
FIG. 10 shows a PCB heater in the main housing.
Figure 11:
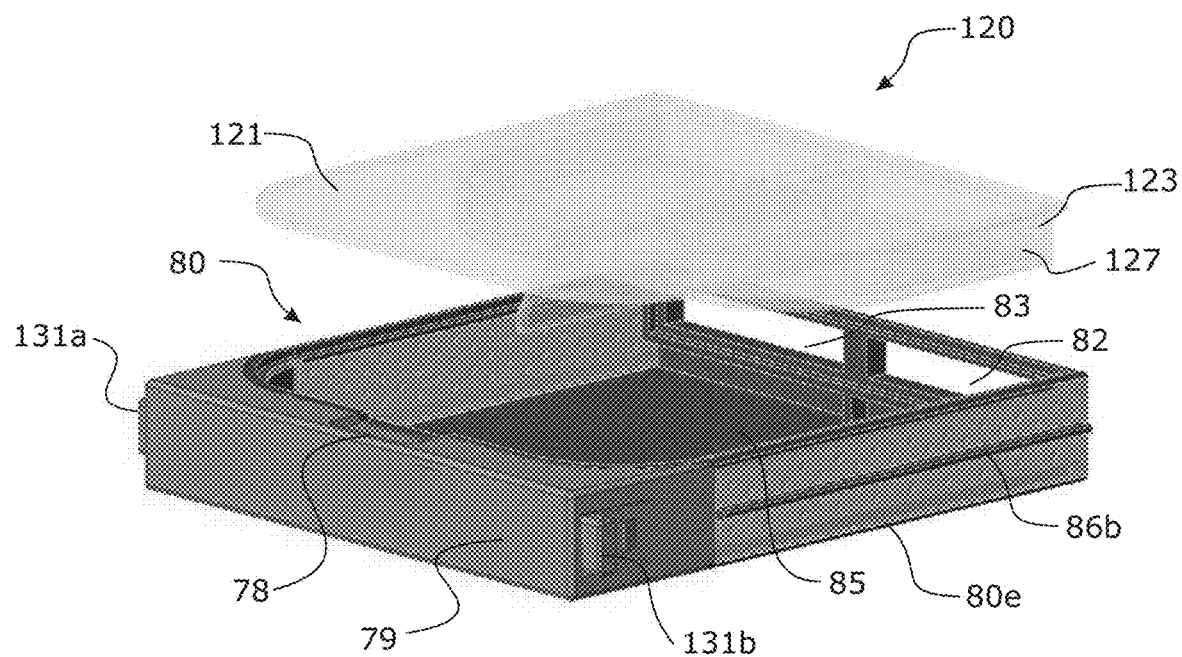
FIGS. 11 to 13 show the water cartridge chamber and lid.
Figure 12A:
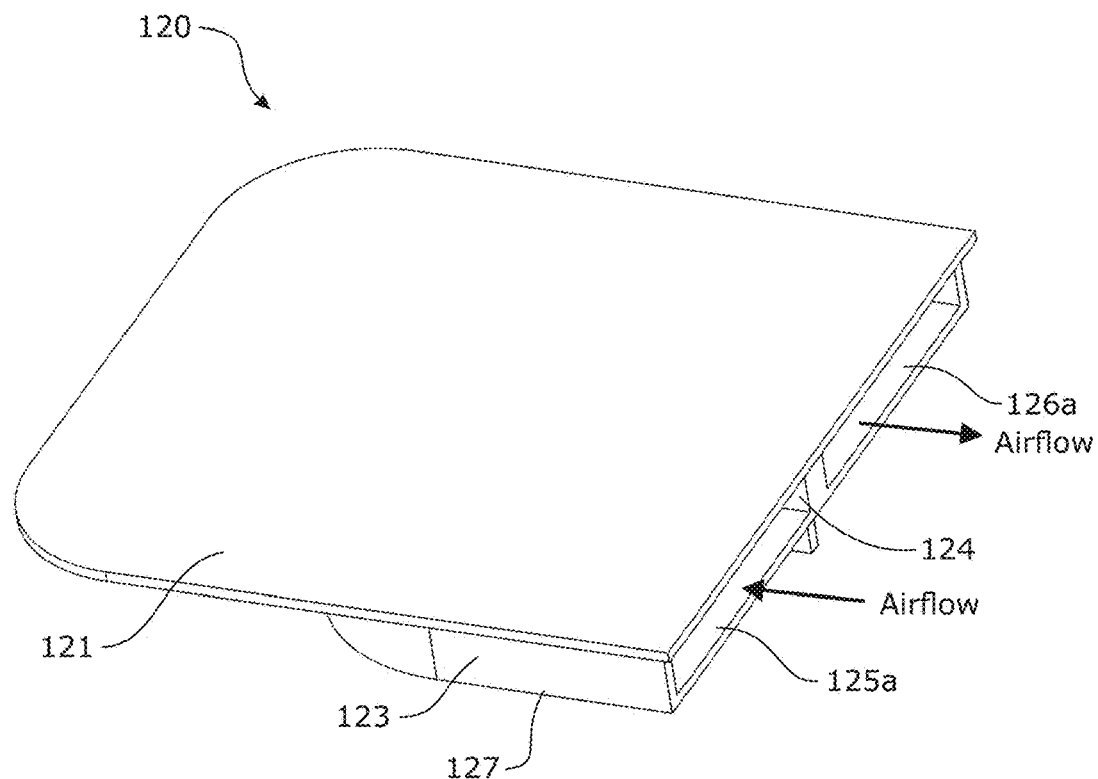
Figure 12B:
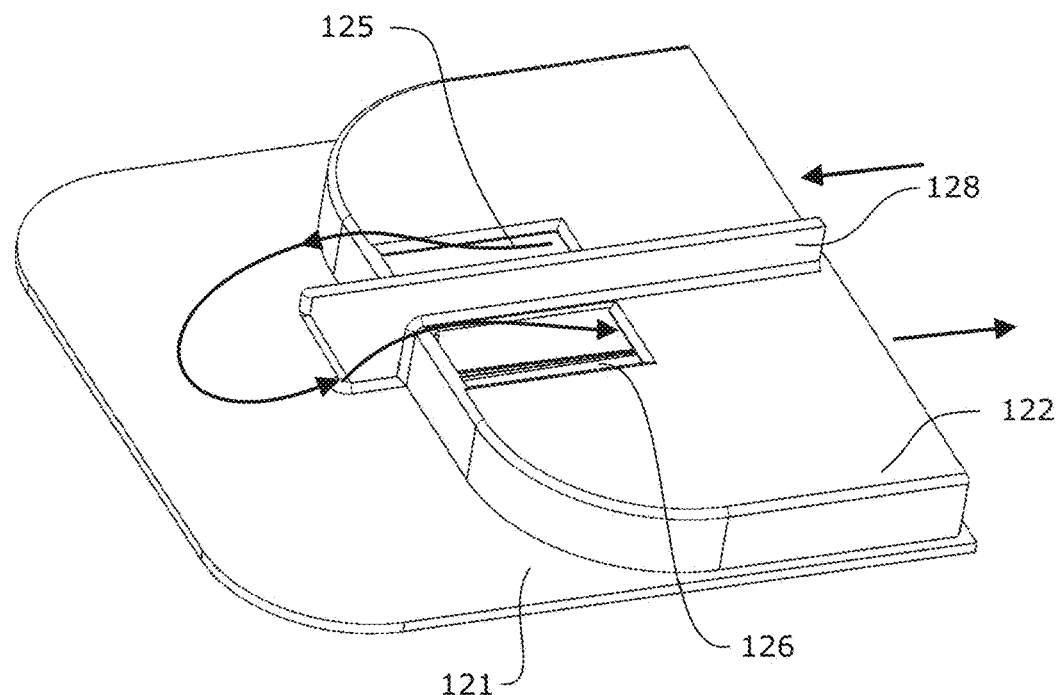
Figure 13:
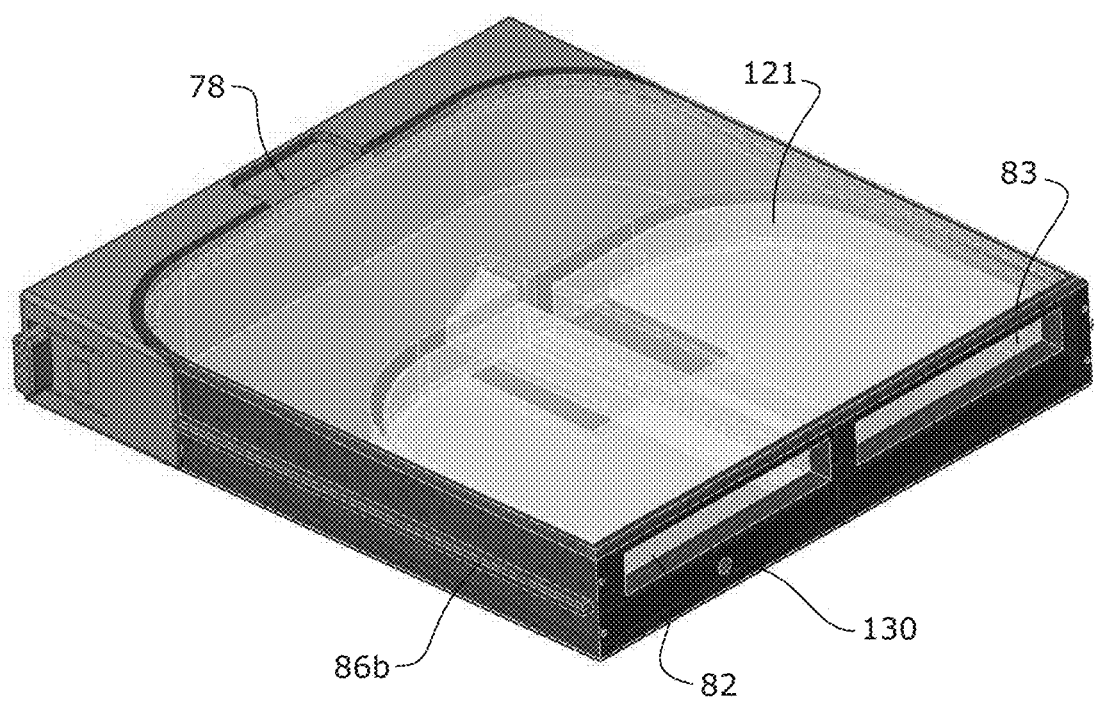
Figure 14:
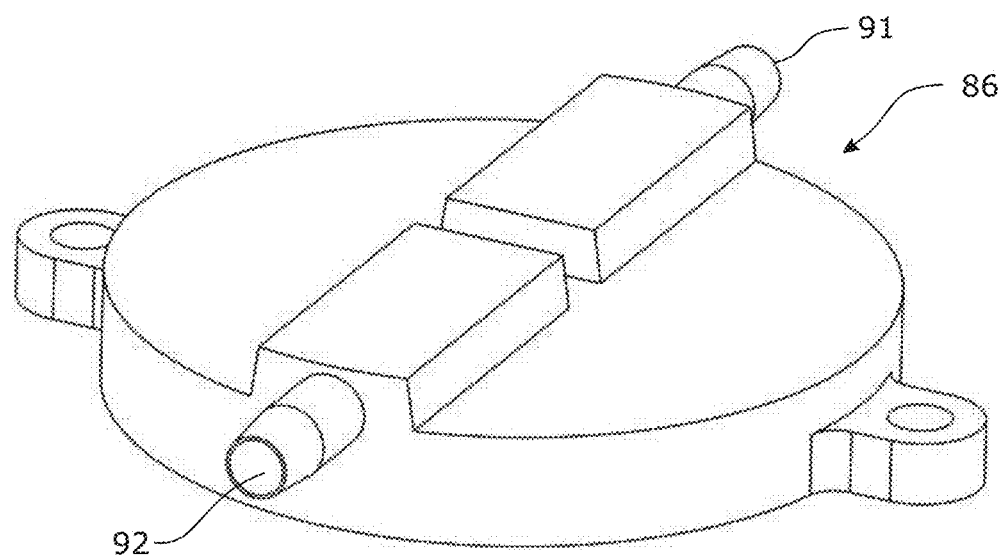
FIG. 14 shows a pump of the respiratory therapy system.

As shown in FIG. 10, the slot 88 in the main housing base portion 70a comprises a heater plate 135 (or other heater source), preferably in the form of the PCB heater. The PCB heater comprises a tortuous path electrical track 138, with an intrinsic resistance. Applying voltage and/or current to the track via terminals causes resistance heating. The voltage and/or current is applied via terminals in the slot 88 that couple directly or indirectly to corresponding terminals on the PCB and/or cartridge when the cartridge is inserted in the slot. The terminals could be at any suitable location in the slot (side, back or bottom for example) to contact the PCB. It will be appreciated that instead of terminals, contacts, connectors, wires or the like can be used. The voltage/ current is provided from the controller 60 or alternatively directly by a power source as described elsewhere herein. When the water chamber cartridge 80 is inserted into the slot 88, the heat conductive base 80e of the chamber cartridge 80 couples to the PCB heater 135 in a heat conductive manner to transfer heat from the PCB heater into water in the chamber 85 in order to heat the water. Together, the water chamber cartridge 80, slot 88 and/or PCB heater plate (alone or in combination) form part or all of the gases humidifier 300. The water chamber cartridge and/or heater source comprise a sensor(s) (shown as 65b, 65c in FIG. 7a) to sense temperature, humidity, flow, pressure or other parameter of the water or gases in the humidifier. Alternatively, these could be in the gases flow path. The output from the sensors is provided to the controller 60 to enable operation of the humidifier 300 based on the sensor output, as required.

The heater source 135 is also coupled directly or indirectly (e.g. via the controller) to an external or internal power source 61. This could be the same power source 61 for the controller 60, or another power source. The controller 60 is coupled to and operates the heater source (by controlling power to the heater source) optionally based on output from one or more of the sensors 65a to 65c. In a preferred variation, the controller 60 provides the power to the heater source. A safety mechanism can optionally be provided to switch the power off if the tray is disengaged and the heater is accessible.

Preferably, during use, there is a nominal amount of water in the water chamber 80, an amount that is spread thinly over part or all of the chamber base 80e. This is to improve heat transfer rate to the water. As previously described, the base 80e of the humidifier chamber cartridge 80 could comprise micro-channels or other configurations to promote water spreading. Additionally, there might be a hydrophilic coating or other type of coating which promotes water spreading on the base 80e to improve heating rate of the water in the chamber 85. Preferably, the depth of the water is a maximum of 2 mm, although that is not essential. There could be a maximum of 3 mm or some other depth that is suitable. Those skilled in the art will understand there is an optimisation between spreading the water thinly to improve heat transfer, but not spreading so thinly such that there is not suitable coverage of the water and proper thermal coupling between the water and the heater/conductor plate. As such, other depths of water could be envisaged. Controlling the depth of water also provide mitigation against spilling/backflow if the chamber, humidifier or entire system is tilted. A shallower water level allows for more tilting before spillage/backflow occurs.

Figure 9A:
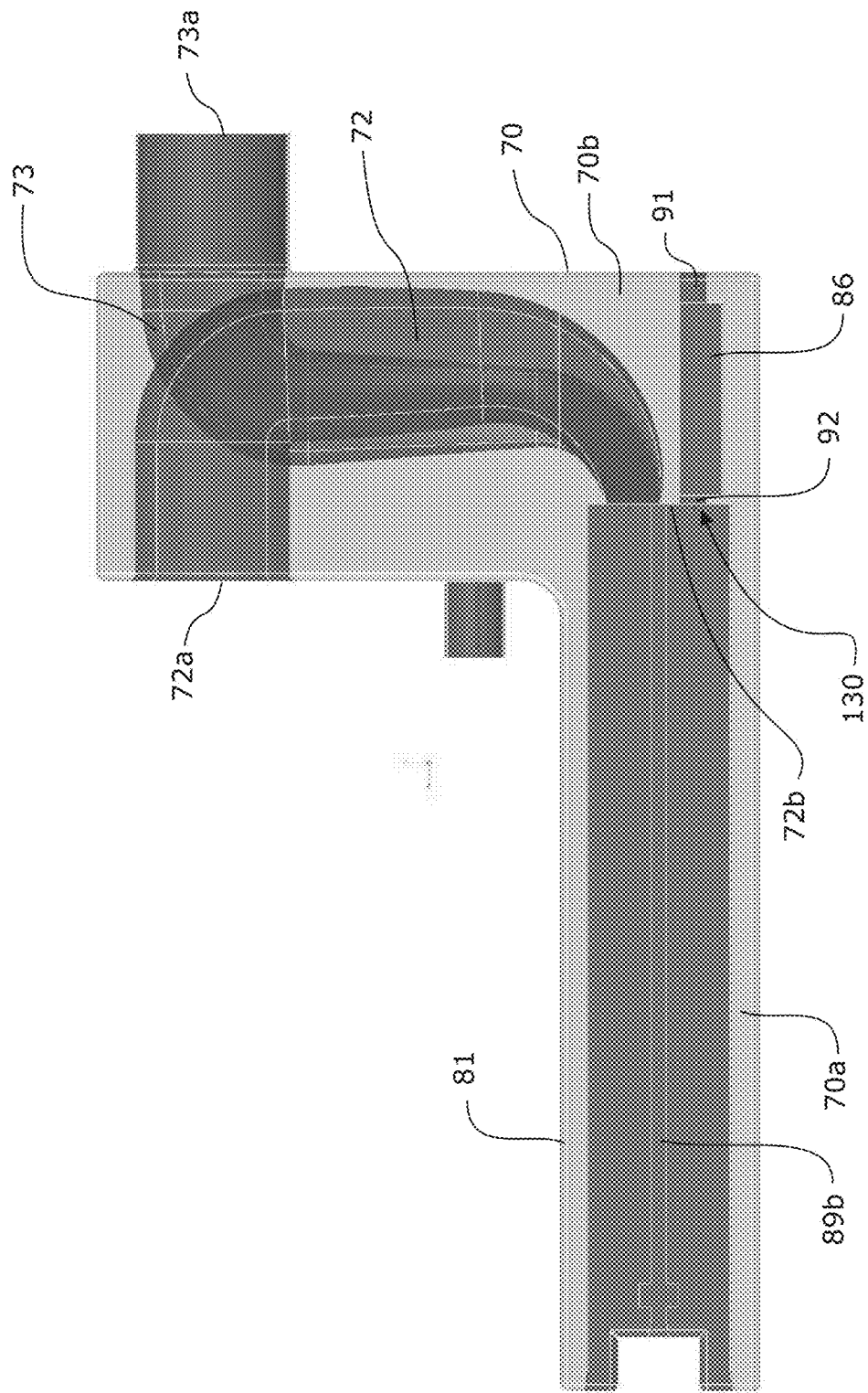
FIGS. 9A, 9B show the main housing of the respiratory therapy system.
Figure 9B:
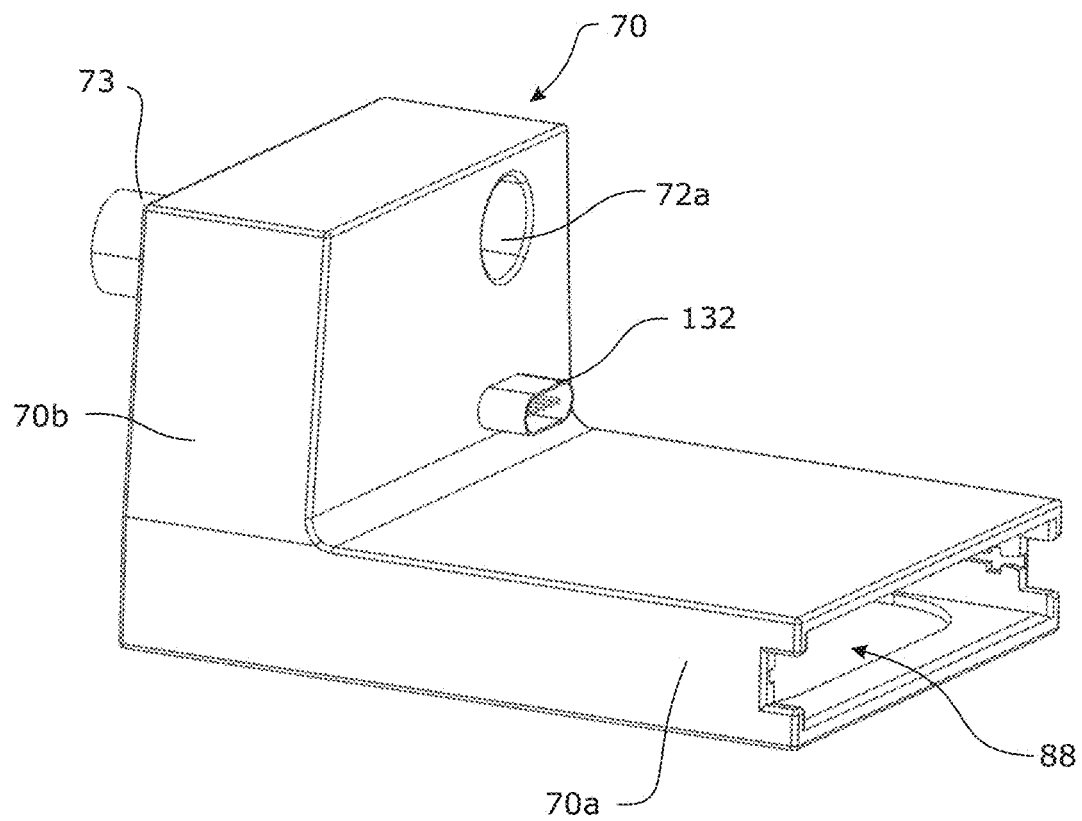

The main housing 70 is shown in isolation in FIGS. 9A, 9B. The upright portion 70b of the respiratory therapy system main housing 70 holds a humidifier inlet conduit 72 which fluidly couples the outlet 204 of the flow generator 200 to the inlet 82 of the water cartridge chamber 80 to allow a passage of gases from the flow generator 200 to the water chamber 85 for humidification. The inlet conduit 72 comprises an inlet 72a (see FIGS. 9A, 9B) formed in or extending through the upright portion housing 70b, and configured for coupling to the outlet 204 on the flow generator housing 200. Preferably, the inlet 72a of the humidifier inlet conduit has a circular cross-section and is formed in and/or extends through the upright portion 70b of the housing. The other end of the humidifier inlet conduit 72 is shaped with a (preferably oblong/rectangular) cross-section outlet 72b to match/correspond with the inlet opening 82 shape on the back wall 80d of the water chamber cartridge 80. There is a seal between the rectangular outlet 72b of the humidifier inlet conduit 72 and the inlet 82 to the water chamber 85 to prevent or reduce gases leakage so that the gases flow from the flow generator enters the water chamber 85. The seal can also prevent or reduce water leakage.

The upright portion 70b of the respiratory therapy system main housing 70 also comprises a respiratory system outlet conduit 73 that fluidly couples the outlet 83 of the water chamber 85 to the outlet 73a of the respiratory therapy system to allow passage of humidified gases from the water chamber 85 to the outlet of the respiratory therapy system, for transfer to a patient via a breathing (gases) conduit 112 (e.g. heated or non-heated breathing tube) and patient interface 116. Preferably, the outlet 73a of the respiratory system outlet conduit 73 has a circular cross-section, for a connection directly or indirectly to a breathing conduit 112/patient interface 116 (see FIG. 1). Preferably the outlet 73a is formed in and/or extends through the upright portion 70b of the main housing. The other end of the outlet conduit 73 is shaped with a (preferably oblong/rectangular) cross-section inlet 73b to match/correspond with the outlet opening 83 shape on the back wall 80d of the water chamber cartridge 80.

There is a seal between the rectangular inlet 73b of the respiratory system outlet conduit 73 and the outlet 83 of the water chamber 85 to prevent or reduce leakage so that the gases flow from the chamber flows to the respiratory system outlet 73a. Preferably the seals on the inlet/outlet of the back wall of the water chamber cartridge are chamfered vertical seals positioned at the airflow openings. Alternatively, a seal could be on the cartridge 80 exterior to achieve sealing. The cross-section of the water chamber inlet 72 and respiratory system outlet 73 conduits transition from an oblong/rectangular cross-section to a circular cross-section. The cross-section at each point in the conduit can take the necessary configuration to ensure that the cross-sectional area remains constant throughout the conduit, if required.

The vertical arrangement of the inlet 72 and outlet 73 conduits, and the placement of the flow generator 200 above the humidifier 300 reduces the chance of water ingress from the humidifier into the flow generator 200, controllers, blower and/or patient breathing tube 116/patient interface 112 (patient circuit).

The housing 70 also comprises a metering arrangement/device 86. In this embodiment, the metering device is a pump 86, such as a micro pump, gravity fed pump, peristaltic pump, piezo pump (double or single with or without a valve) or any other pump described herein, at the rear of the main housing 70. The pump 86, which is shown in more detail in FIG. 14, has an inlet 91 exposed though the rear wall of the main housing 70, and an outlet 92 from the pump fluidly couples through the opening/water inlet 130 in the back wall of the water chamber cartridge 85. There is a seal between the pump outlet 92 and the inlet 130 into the water chamber cartridge. This is a preferred arrangement of the pump, although it will be appreciated that other pumps and configurations are possible. The pump (optionally in combination with the controller) provides a water metering arrangement/device. In an alternative, the metering device could be an electronic valve, which would be used instead of a pump.

The main housing 70 has the connector 132 with pins for interconnection with the connector 133 on the flow generator and therefore transfer of power and/or data/signals to/from the main housing and the flow generator. As the main housing 70 contains the humidifier and optionally sensors, this allows for power and signal transfer between the various sensors 65a to 65c, the power source 61, the humidifier 300, the flow generator 200, user interface 62 and the controller 60 to enable control and operation of the system.

As previously described, the respiratory system 100 can have one or more suitable power sources 61 for operating the controller and/or providing power for the heater source and/or blower. The power source can be internal in the main housing 70, or elsewhere in the system 100. It alternatively can be external. The power source might comprise multiple separate power sources. In one option, the power source 61 is formed from an internal or external battery source that is charged from an external or internal mains power supply. In this case the battery could be the power source, or both the battery and power supply could be deemed the power source. In one option, shown in FIG. 7A, the power source 61 for the controller 60 and blower 201 is an external mains power supply that is coupled to the flow generator housing 71. The power source for the pump 86 and the heating source 135 is an external power supply that is coupled to the main housing 70. In another option, the respiratory therapy apparatus 100 is powered generally from a mains power supply and transmits this power to operate the flow generator 200 via the connection port 133/terminal arrangement 132 with power pins. The power pins are formed and/or protrude through the main housing 70 on the upright portion 70b, and the pins are energised from the power supply. The flow generator housing 201 has a corresponding port 133 that can electrically engage with the pins 132. When the flow generator housing 71 is introduced into the base portion 70a, the port 133 aligns and engages with the power pins terminal 132 and connects when the flow generator housing 200 is slid into position. Power from the power supply can then be transferred to the flow generator 200 for operation. The port 133/terminal 132 arrangement could also comprise signal connectors, although these could optionally be separate. In an alternative, the flow generator could be powered directly from the power supply and transmit the power to the flow generator housing 71 and/or humidifier via connection ports. Alternatively, inductive power transfer could be used also or instead of the arrangement above.

In an alternative embodiment, the PCB heater plate 135 could be integrated into the water chamber cartridge. For example, it could form part of the base.

In an alternative embodiment, an electrically conductive polymer (ECP) could be used as a heater source 135 for heating. The ECP could be a structure/material such as that described in US 2015/0265796 (which is incorporated herein by reference in its entirety) also filed by the same applicants. Either, an ECP structure, e.g. in the form of a heater plate 135, could be substituted for the PCB heater as previously described, and a heat conductive heater plate used in the water chamber cartridge; or alternatively, the ECP could be moulded into or form part of the bottom of the water chamber cartridge. Alternatively, or additionally, ECP can be overmoulded a PCB with conductors to provide power to the ECP for heating. Further or alternatively, part or all of the chamber cartridge could be formed of ECP, and energised to create the heater source. The ECP could be coupled to any power source previously described. In another variation, the heater source could be a ceramic or flexible element.

Where the heater source is integrated into or forms part of the water chamber cartridge (e.g. where the chamber is ECP or the PCB is the base), power pins 137a to 137d are located in water chamber slot/compartment to power directly to water chamber via corresponding power pins 136a to 136d on the chamber. These pins could be located on any of the internal surfaces of the slot (side, back or bottom) to make contact with the respective part(s) of the water chamber. Power can be transferred to the heater source via the pins 136a to 137d.

Figure 16:
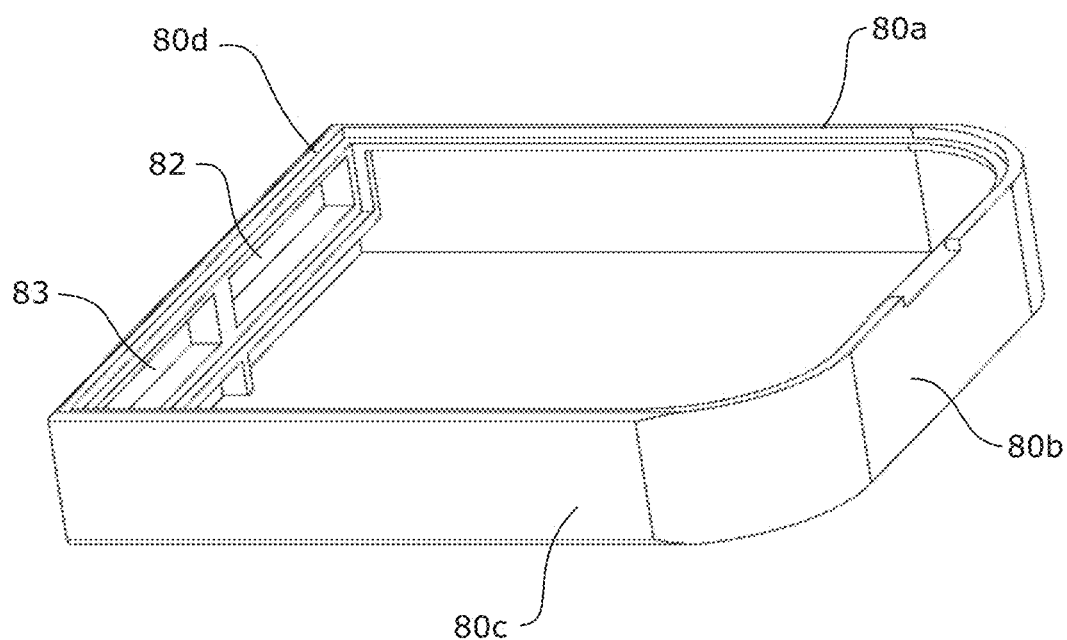
FIGS. 16 to 18 show an alternative water chamber cartridge formed of ECP.
Figure 17:
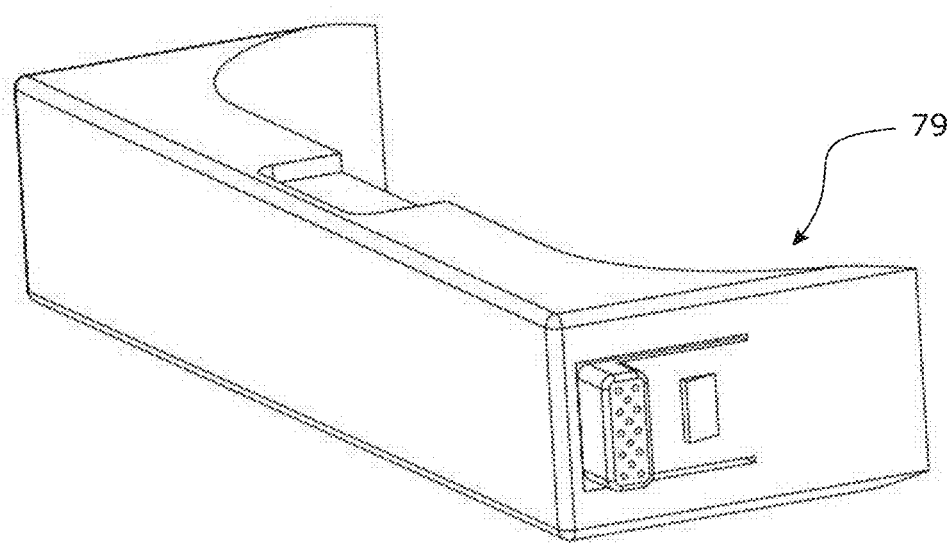

For example, FIGS. 16 and 17 show an alternative water chamber cartridge that is formed as an ECP chamber. The walls of the chamber are formed from ECP and can be coupled to a power source such that the walls and/or base form the heat source. In this case, no PCB or other heater plate is required, although optionally the base could be ECP or some other heat source to provide a heater plate also. As the ECP wall will become hot, the front comprises an (optionally) detachable fascia 79 (see FIG. 17) formed from a non or low-thermally conducting material or (thermally insulating material). This protects a user when touching the cartridge—e.g. when removing the cartridge from the housing 70.

FIGS. 19 to 22 shows yet a further alternative water chamber cartridge (the main housing and some components are shown, but most other components are omitted for clarity). In this variation, the cartridge 80 is formed with walls in the same way as previously (preferably as ECP), however the interior region 85 is formed as a bowl 185. Water ingress is through an opening 130 via the pump 86 and settles in the bowl.

The lid 180 comprises a top plate 181 that sits on the side walls 80a to 80d on a perimeter recess of the water chamber cartridge 80 in a manner similar to that previously described. A baffle 182 is suspended below the top plate. An annular bottom plate 183 is suspended from the top plate via a sloping wall 184 that is curved and sloped commensurate with the curvature and slope of the bowl 185 so that when the lid 180 is seated in the cartridge 80, the wall and bottom plate will sit within the bowl. The curved wall 184 does not extend all the way around the perimeter of the circular bottom plate 183, but rather is open. A central dividing wall 186 extends between the top plate 181 and the bottom plate 183 to divide the baffle 182 into first and second sections with a corresponding inlet 187a and outlet 187b that correspond and align with an inlet 185 and outlet 186 on the back wall of the water chamber cartridge 80, in a similar manner to the previous embodiments.

Two curved a walls or fins 188a, 188b are suspended from the bottom of the bottom plate 183 and a dividing wall/fin/baffle 189 extends between the two at right angles. This wall 189 and the central wall 186 divide the annular opening in the bottom plate 183 into two separate openings 190a, 190b. The dividing wall 189 has a curved bottom commensurate with the curve on the bottom of the bowl 185. When the lid is in place on the chamber cartridge, the dividing wall 189 will sit on the bottom of the bowl 185 to partially divide the bowl into two regions.

During use there is a gas flow path (see "airflow" arrows) from the inlet 82 of the cartridge chamber through the inlet opening 187a through the first opening 190a in the bottom plate 183 around the curve dividing walls 188a, 188b up through the second opening 190b in the bottom plate through the outlet 187b and then through the outlet 83 of the chamber 80. The gases flowing along this path will collect moisture that sits in the bottom of the bowl 185 and become humidified. An advantage of the bowl arrangement is that if the chamber 80, or system as a whole, is tilted, there is still a flat surface of water for the gas flow to flow over. The chamber could have any heating source 135 previously described, such as an ECP heat source.

Operation of the device will now be described. This can apply to the embodiments above. The water chamber cartridge 80 is assembled with the lid and then inserted into the main housing 70 by sliding the water chamber cartridge 80 into the slot 88 on the rail/channels. The inlet 82 and outlet 83 openings fluidly couple to the humidifier inlet 72 and respiratory therapy outlet 73 conduits; and the water inlet 130 of the water chamber 85 fluidly couples to the outlet 92 of the pump 86. The flow generator 200 is slid or otherwise installed on to the main housing 70 and the outlet 204 of the flow generator 200 is sealingly coupled to the inlet 72*a* of the humidifier inlet conduit 72. Also, the power and/or data/signal port/connector 133 of the flow generator 200 is coupled electrically to the terminals of the connector 132 on the respiratory therapy system main housing 70.

A water source 69 (fluid supply) is coupled to the inlet of the pump 86. The water supply 69 could be a bottle, container, bag, reservoir or the like, or even a tap/faucet connected to a mains water supply. A filter could be provided to filter the water, for example to remove bacteria. A water level meter can be provided. Preferably, the water supply is gravity fed. The pump 86 is coupled to the water supply via a conduit, such as a fluid tube. The pump can block the flow of water if required if the water supply is in a high position. The water supply is preferably separate to the system 100, but could optionally form part of the system. In an alternative, the flow generator, humidifier cartridge chamber and/or water source could be installed in a different order. A breathing conduit 112 (e.g. heated breathing tube) is connected to the outlet 73*a* and patient interface 116 is connected to the conduit.

The respiratory therapy system 100 can then be switched on and operated using the user interface in the usual manner. Under control by the controller 60 and where required based on sensor 65*a* to 65*c* output, the flow generator 200 (by way of the blower) will create a flow of gases in the usual manner for a respiratory therapy system and the gases will flow through the humidifier inlet conduit 72 into the water chamber 85 for humidification. The controller operates the pump 86 to provide a metering arrangement to transfer water from the water reservoir to the water chamber 85. This creates a thin layer of water over some or all of the base 80*e* of the water chamber (or in the bowl if that is present), preferably at a maximum of 2 mm of depth, or other depth as previously described. The controller operates the heater 135 (either by energising the PCB heater and/or energising the ECP) to create a heat which is then transferred through the base 80*e* (or walls as where that is the embodiment) of the water chamber cartridge 80 to heat the thin layer of water. Gases from the flow generator 200 passes over the water, and absorbs moisture, thus humidifying the gases. The gases then flow out through the outlet conduit 73 for delivery to the patient through a breathing conduit 112 and patient interface 116 in the usual manner.

Variations to the embodiments described above are possible. For example, power source(s) 61 can take various forms (mains, battery, or both, for example) and can be positioned in various locations, externally and/or internally. For example, the humidifier module 300 might house (or connect to if external) the power source 61 to power the flow generator 200 and humidifier 300 and pump 86, or alternatively the flow generator might house (or connect to if external) the power source 61 to power the flow generator 200 and humidifier 300 and pump 86. In yet a further alternative, the main housing 70 might house (or connect to if external) the power source to power the flow generator and humidifier. A battery power source can improve provide cost, convenience and travelling benefits.

In another variation, the controller 60 can reside in other parts of the system 100, such as the humidifier 300 or the main housing 70. Alternatively, there could be two or more controllers, in the flow generator, humidifier, main housing or elsewhere.

The sensors can be located in any suitable location to measure parameters (ambient or otherwise), relative or absolute for use in control and operation of the system. As a further example, tilt sensors, water level sensors water flow sensors, water presence sensors (splash sensors), engagement detection sensors (e.g. for detection engagement of the flow generator, water chamber cartridge, power source, pump, water supply and or any other component) can be disposed in the humidifier (or in the chamber of the humidifier) or any other suitable part of the system 100.

In another variation, the metering device (such as pump or valve) 86 could be near the water supply and optionally external from the system 100.

The connector pair 132/133 can carry data/signals and/or power. Or, alternatively, separate connector pairs could be used, one for data/signals, and one for power.

In another variation a tilt/orientation sensor can be provided and/or sensors on or around the heater to detect water presence. The controller can use this input to provide a spillage warning to a user.

Some configurations described (or some aspects or combinations thereof) provide a small and portable device. This is further assisted by the modular configuration and a preferably separate water supply. The thin layer of water to be heated can increase humidification response time. The configuration of the chamber and inlet/outlets and conduits reduce the risk of water ingress into the flow generator and/or electrical parts of the system.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A gases humidifier comprising:
a humidification chamber adapted to vaporize fluid, the humidification chamber comprising a heater adapted to heat the fluid;
a metering arrangement adapted to transfer fluid from a fluid supply to the humidification chamber, wherein at least a part of the metering arrangement lies within the gases humidifier, wherein the metering arrangement comprises a pump; and
a thermally conductive element positioned over the heater, wherein the humidification chamber defines a cavity adapted to accept the thermally conductive element, wherein the thermally conductive element is slideable relative to the heater when inserted into the cavity.

2. The gases humidifier of claim 1, wherein at least a part of the metering arrangement lies within the humidification chamber.

3. The gases humidifier of claim 2, wherein only an outlet of the metering arrangement lies within the humidification chamber.

4. The gases humidifier of claim 1, wherein the metering arrangement is configured to transfer liquid directly to the thermally conductive element.

5. The gases humidifier of claim 1, wherein an outlet of the metering arrangement is positioned directly over the thermally conductive element.

6. The gases humidifier of claim 1, further comprising a locking engagement arrangement configured to retain the thermally conductive element within the cavity.

7. The gases humidifier of claim 6, wherein the locking engagement arrangement comprises open and closed positions, and wherein the locking engagement arrangement may be detached from the gases humidifier when in the open position to allow access to the thermally conductive element.

8. The gases humidifier of claim 1, wherein the heater is stationary relative to the cavity.

9. The gases humidifier of claim 1, wherein the thermally conductive element comprises fins or baffles.

10. The gases humidifier of claim 1, wherein the heater is configured to generate heat which in turn is transmitted through the thermally conductive element to heat fluids present on the thermally conductive element.

11. The gases humidifier of claim 1, wherein the humidification chamber comprises a structure adapted to force or urge the thermally conductive element towards the heater.

12. A gases humidifier comprising:
a humidification chamber adapted to vaporize fluid, the humidification chamber comprising a heater adapted to heat the fluid;
a metering arrangement adapted to transfer fluid from a fluid supply to the humidification chamber, wherein at least a part of the metering arrangement lies within the gases humidifier; and
a thermally conductive element positioned over the heater, wherein the humidification chamber defines a cavity adapted to accept the thermally conductive element, wherein the thermally conductive element is slideable relative to the heater when inserted into the cavity, wherein the thermally conductive element comprises a tray.

13. The gases humidifier of claim 12, wherein the humidification chamber comprises rails that guide the sliding of the thermally conductive element into the humidification chamber.

14. The gases humidifier of claim 12, wherein an outlet of the metering arrangement is positioned above the thermally conductive element such that fluids exiting the outlet are deposited onto the thermally conductive element.

15. The gases humidifier of claim 12, wherein only an outlet of the metering arrangement lies within the humidification chamber.

16. The gases humidifier of claim 12, wherein the metering arrangement comprises a pump.

17. The gases humidifier of claim 12, further comprising a locking engagement arrangement configured to retain the thermally conductive element within the cavity.

18. The gases humidifier of claim 17, wherein the locking engagement arrangement comprises open and closed positions, and wherein the locking engagement arrangement may be detached from the gases humidifier when in the open position to allow access to the thermally conductive element.

19. A gases humidifier comprising:
a humidification chamber adapted to vaporize fluid, the humidification chamber comprising a heater adapted to heat the fluid;
a metering arrangement adapted to transfer fluid from a fluid supply to the humidification chamber, wherein at least a part of the metering arrangement lies within the gases humidifier;
a thermally conductive element positioned over the heater, wherein the humidification chamber defines a cavity adapted to accept the thermally conductive element, wherein the thermally conductive element is slideable relative to the heater when inserted into the cavity; and
a locking engagement arrangement, wherein when the locking engagement arrangement is in the closed position, the thermally conductive element is locked in place and the humidification chamber is sealed.

20. The gases humidifier of claim 19, wherein the metering arrangement is configured to transfer liquid directly to the thermally conductive element.

21. The gases humidifier of claim 19, wherein an outlet of the metering arrangement is positioned directly over the thermally conductive element.

* * * * *